(12) United States Patent
Kim et al.

(10) Patent No.: US 10,187,164 B2
(45) Date of Patent: Jan. 22, 2019

(54) MOBILE TERMINAL AND METHOD OF CONTROLLING SAME

(71) Applicant: LG ELECTRONICS INC., Seoul (KR)

(72) Inventors: Cheegoog Kim, Seoul (KR); Mansoo Sin, Seoul (KR); Hyunghoon Oh, Seoul (KR); Jeunguk Ha, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/766,623

(22) PCT Filed: Sep. 27, 2016

(86) PCT No.: PCT/KR2016/010808
§ 371 (c)(1),
(2) Date: Apr. 6, 2018

(87) PCT Pub. No.: WO2017/061722
PCT Pub. Date: Apr. 13, 2017

(65) Prior Publication Data
US 2018/0316442 A1    Nov. 1, 2018

(30) Foreign Application Priority Data

Oct. 7, 2015  (KR) .................. 10-2015-0141004
Sep. 27, 2016  (KR) .................. 10-2016-0123878

(51) Int. Cl.
*H04M 1/00* (2006.01)
*H04B 13/00* (2006.01)
*H04W 4/80* (2018.01)

(52) U.S. Cl.
CPC ............ *H04B 13/005* (2013.01); *H04W 4/80* (2018.02)

(58) Field of Classification Search
CPC .................. H04B 13/005; H04W 4/80
(Continued)

(56) References Cited

U.S. PATENT DOCUMENTS 8,457,595 B2 * 6/2013 MacInnis .......... G06F 17/30598
455/410
9,923,891 B2 * 3/2018 Sydir .................. H04L 63/0861
(Continued)

FOREIGN PATENT DOCUMENTS

KR    10-2005-0103354 A    10/2005
KR    10-2012-0074056 A     7/2012
(Continued)

*Primary Examiner* — Sonny Trinh
(74) *Attorney, Agent, or Firm* — Birch, Stewart, Kolasch & Birch, LLP

(57) ABSTRACT

A mobile terminal and a method for controlling the mobile terminal are disclosed. A mobile terminal according to an embodiment of the present invention, together with an external device separated therefrom, may measure body composition by using human body medium communication. The mobile terminal and the external device have two electrodes that contact areas of a user's body. The mobile terminal outputs a test signal through a first body area contacting a first electrode, and transmits the test signal to the external device through the user's body. The external device generates a feedback signal corresponding to the test signal. The mobile terminal detects a second signal which is the feedback signal that passes through the body and is transmitted through a second electrode. The mobile terminal uses the difference between a reference signal corresponding to the test signal and the second signal to calculate the body composition of the user.

20 Claims, 24 Drawing Sheets

(58) Field of Classification Search
USPC .............. 455/41.1, 41.2, 100, 575.6, 575.7
See application file for complete search history.

(56) References Cited

U.S. PATENT DOCUMENTS

| | | | |
|---|---|---|---|
| 2008/0045854 A1 | 2/2008 | Weichao | |
| 2011/0257546 A1* | 10/2011 | Gozzini | A61B 5/0404 600/509 |
| 2014/0120876 A1* | 5/2014 | Shen | A61B 5/04525 455/411 |
| 2015/0272501 A1* | 10/2015 | MacEachern | A61B 5/0531 600/301 |
| 2015/0358088 A1* | 12/2015 | Eim | H04W 76/14 455/418 |
| 2016/0045135 A1* | 2/2016 | Kim | A61B 5/6843 600/391 |
| 2017/0258376 A1* | 9/2017 | Ram | A61B 5/0507 |
| 2017/0296088 A1* | 10/2017 | Choi | A61B 5/02055 |
| 2017/0331505 A1* | 11/2017 | Shim | H04B 1/385 |

FOREIGN PATENT DOCUMENTS

| | | |
|---|---|---|
| KR | 10-2014-0007994 A | 1/2014 |
| KR | 10-2015-0061100 A | 6/2015 |

\* cited by examiner

【Figure 1】
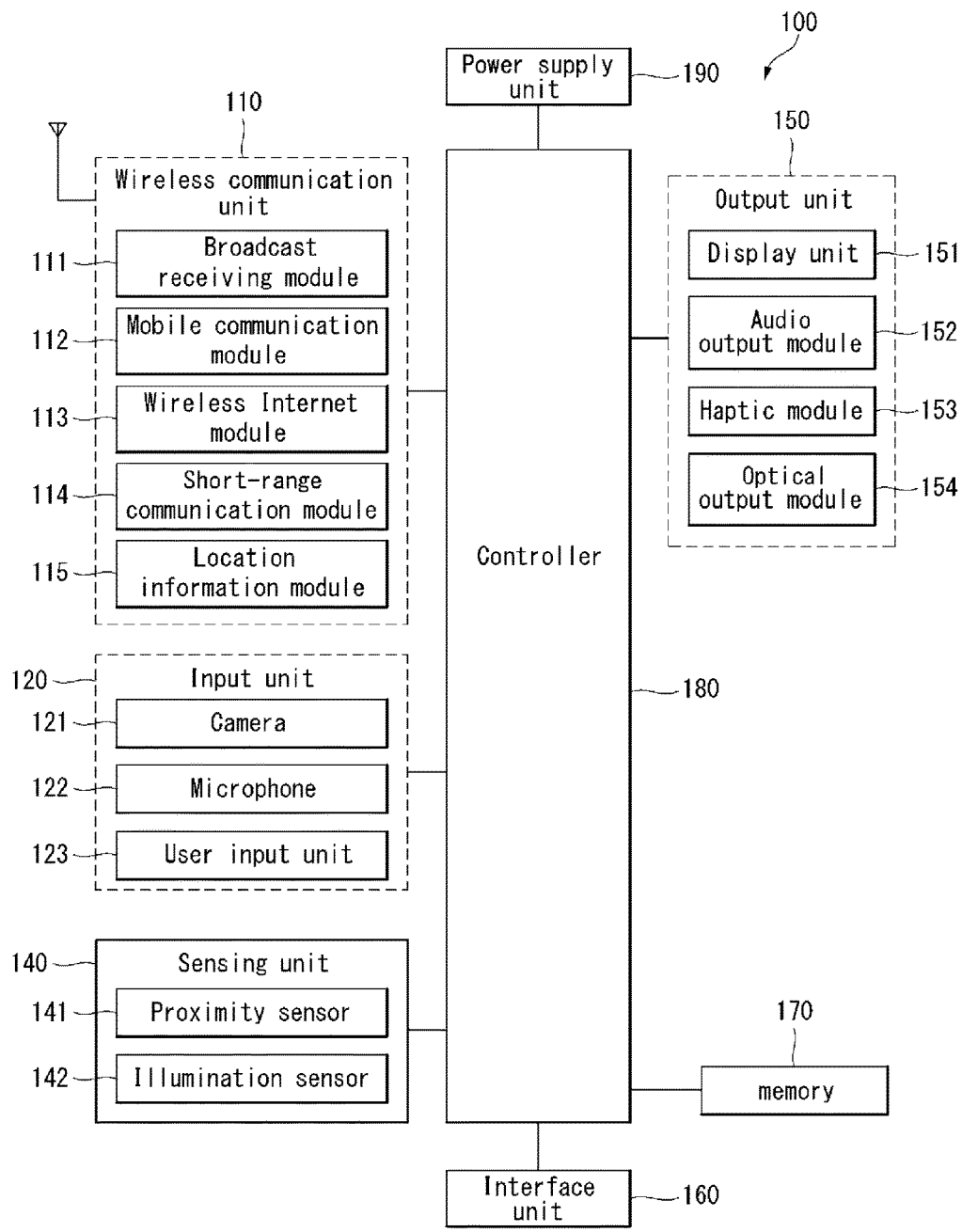

【Figure 2a】
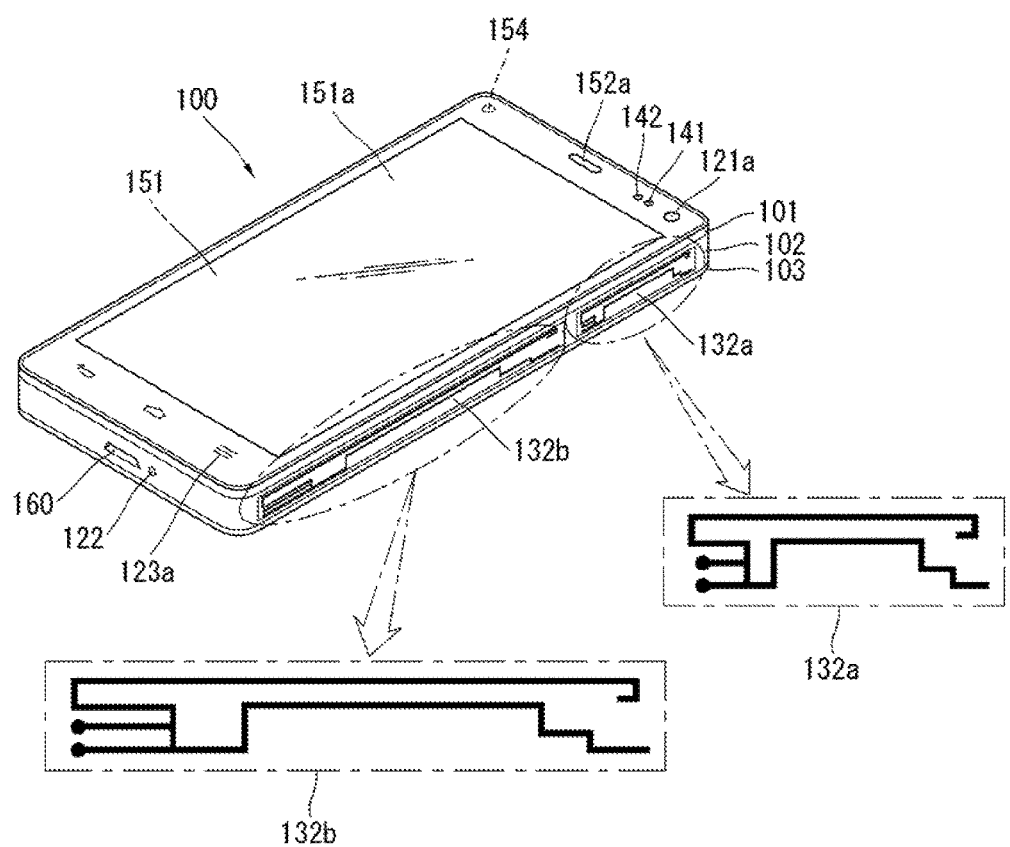

[Figure 2b]
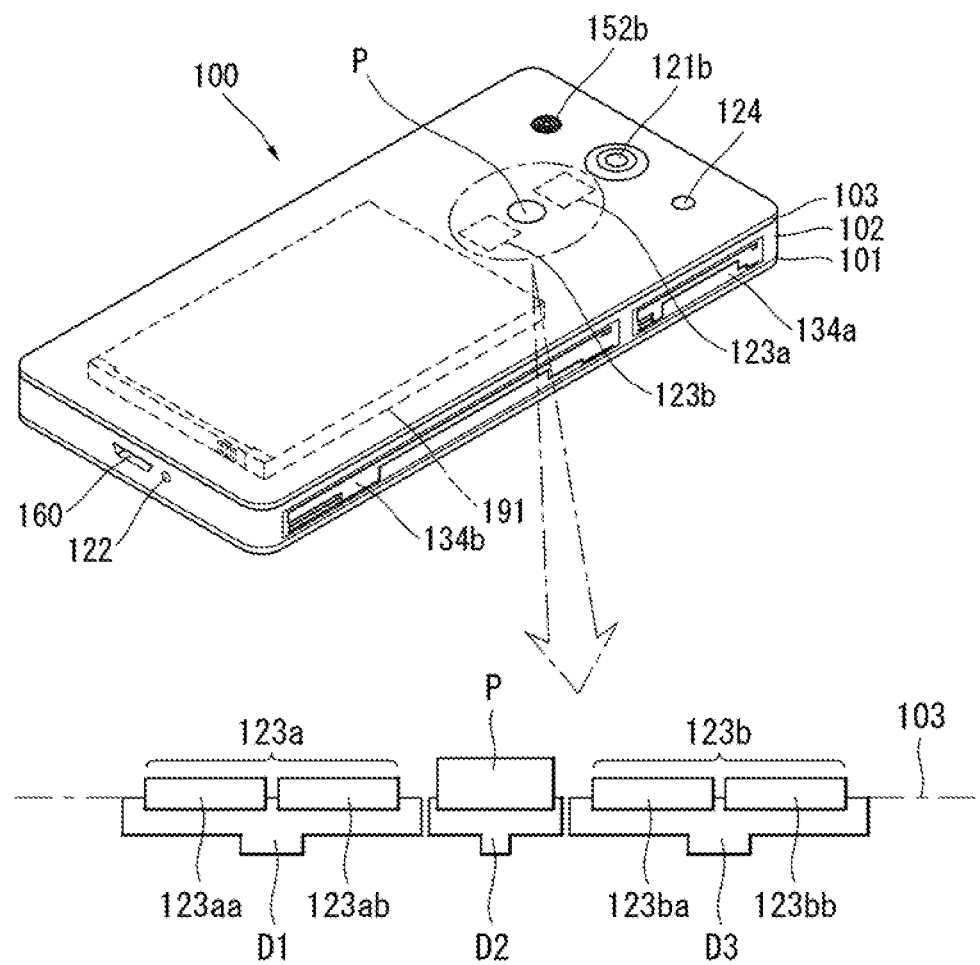

【Figure 2c】
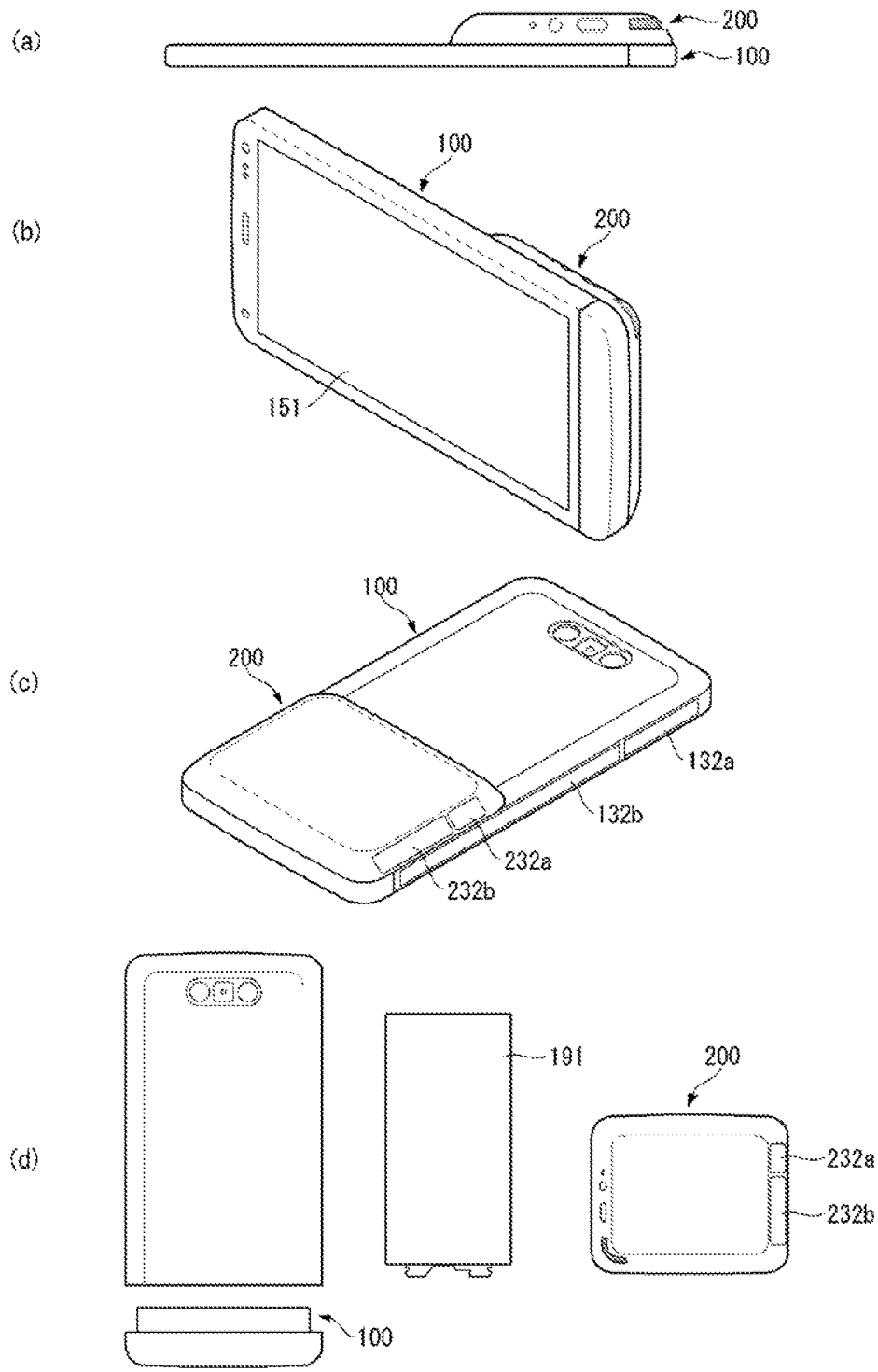

【Figure 2d】
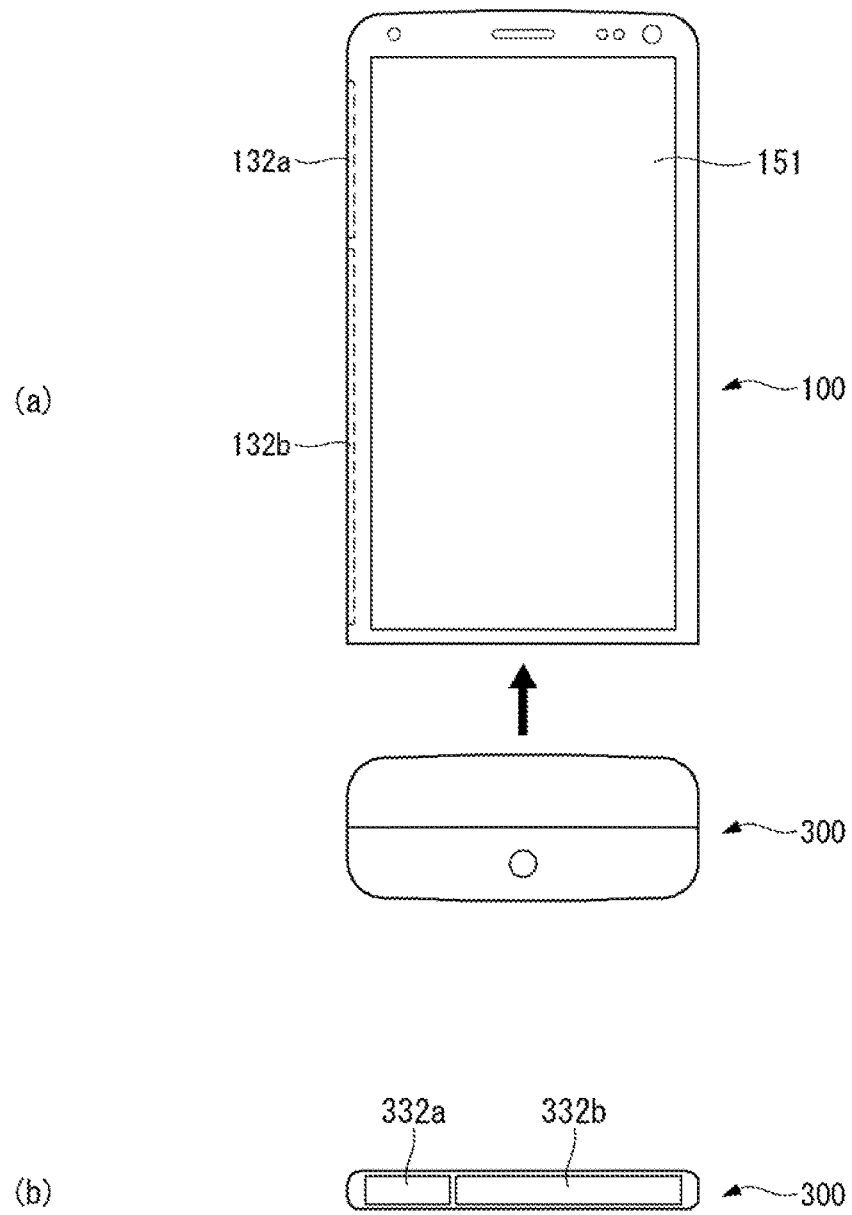

【Figure 3a】
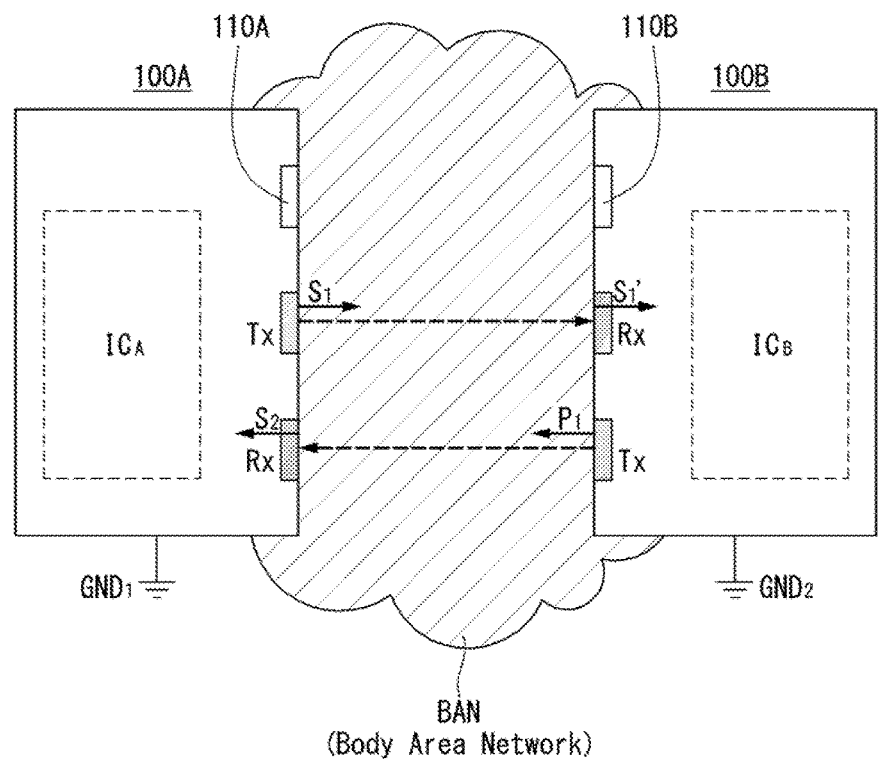

【Figure 3b】
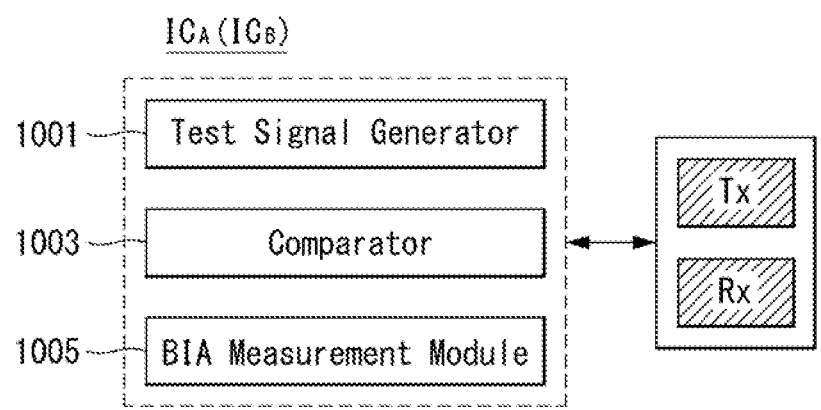

[Figure 4]
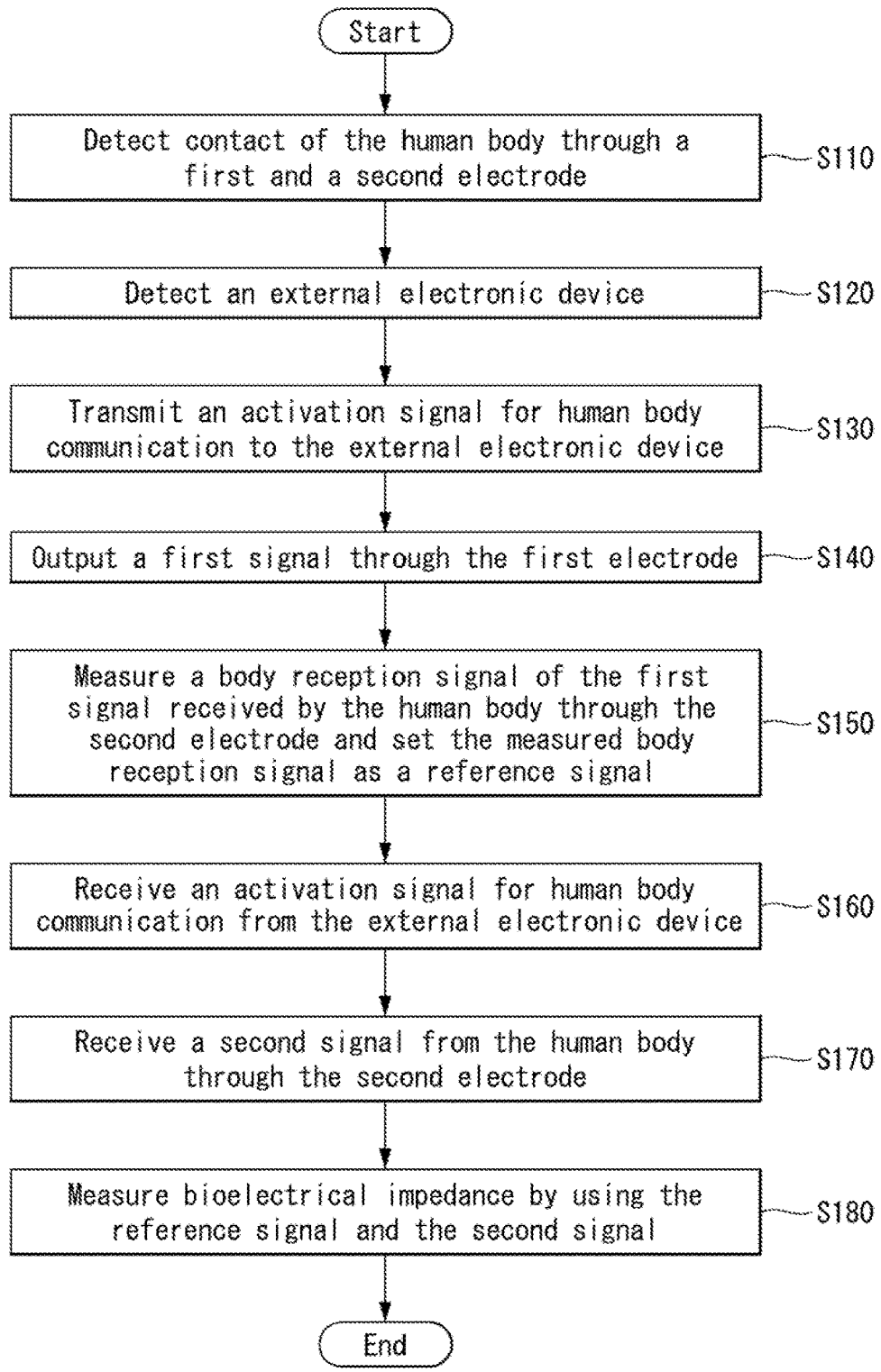

【Figure 5】
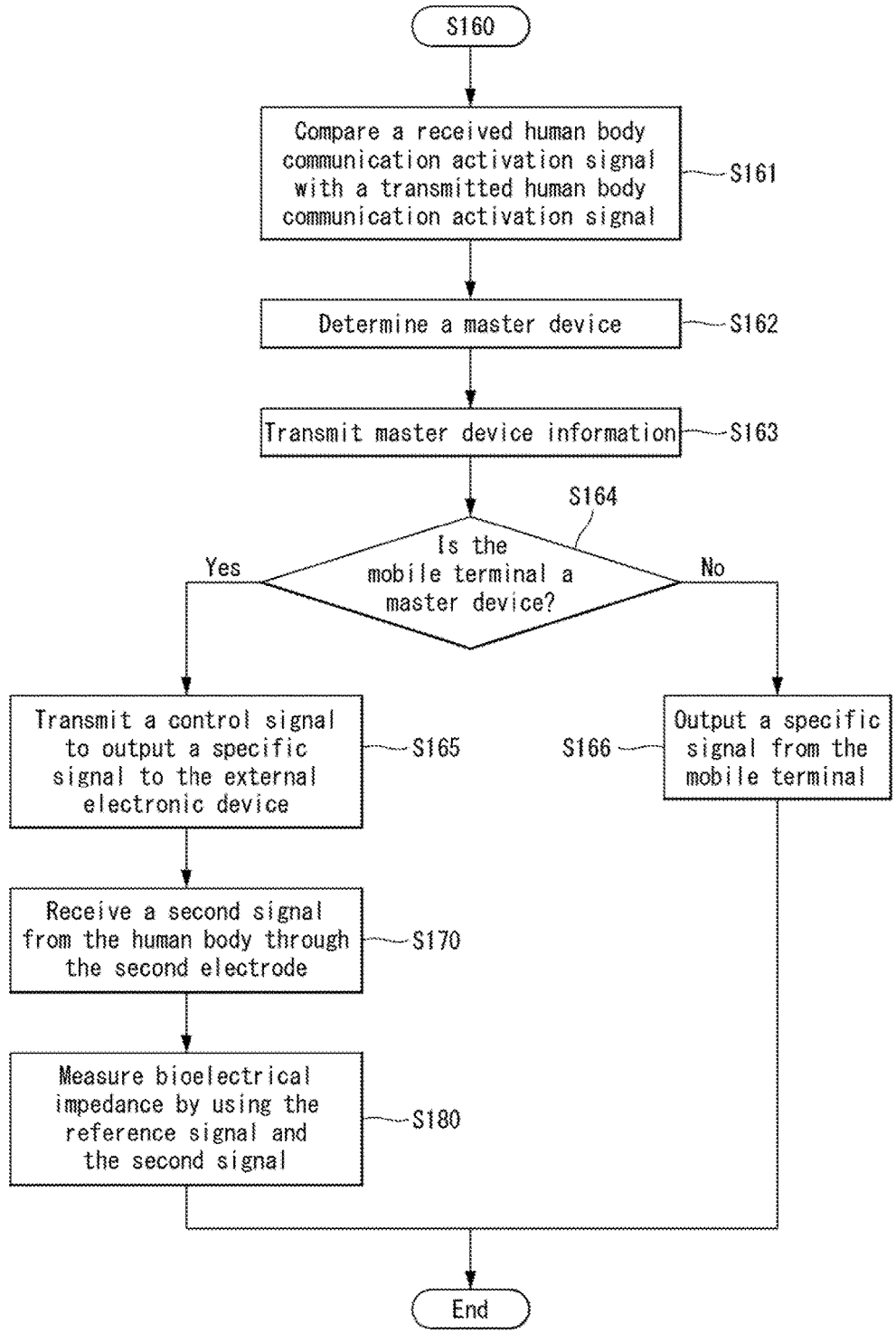

[Figure 6a]
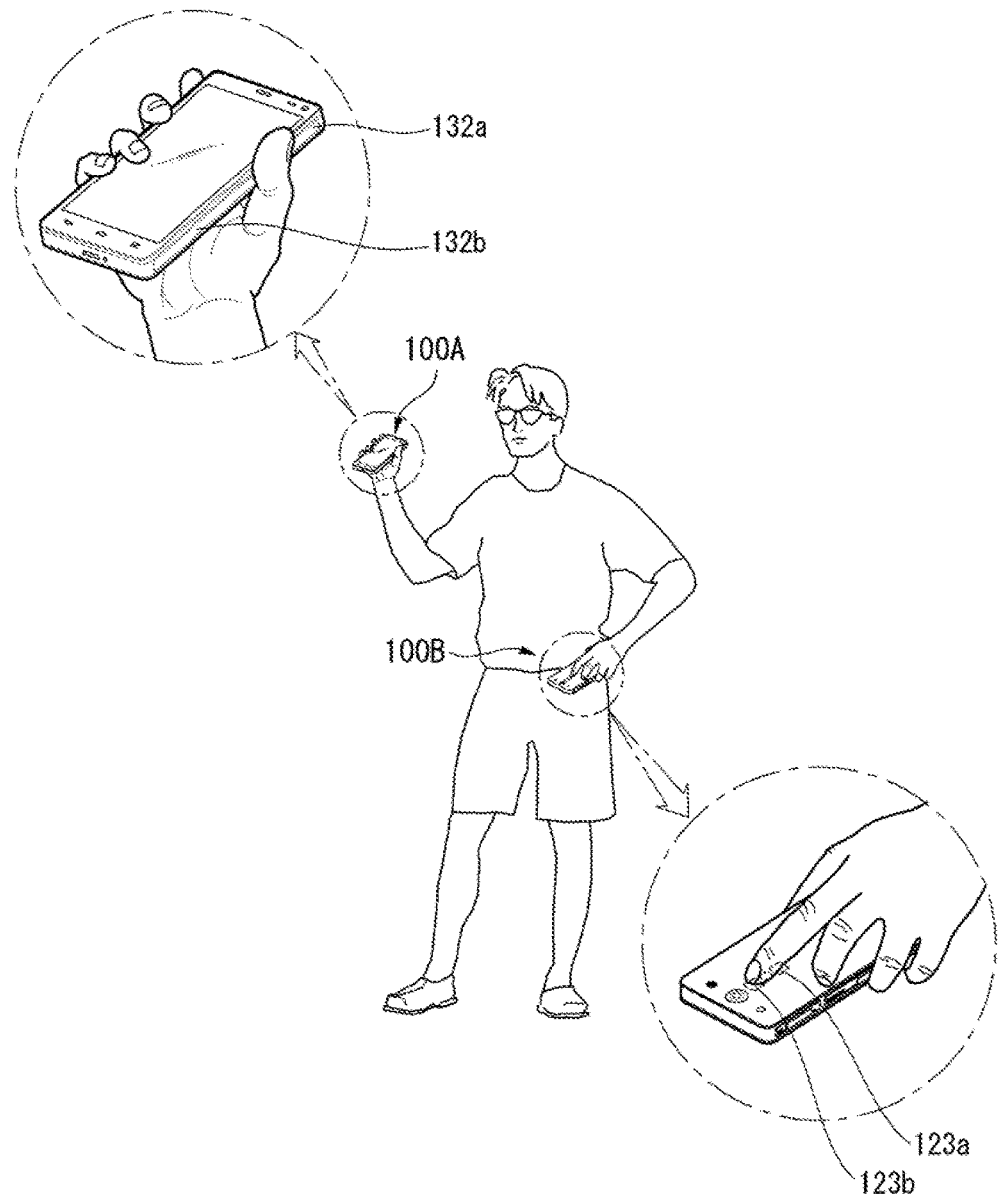

【Figure 6b】
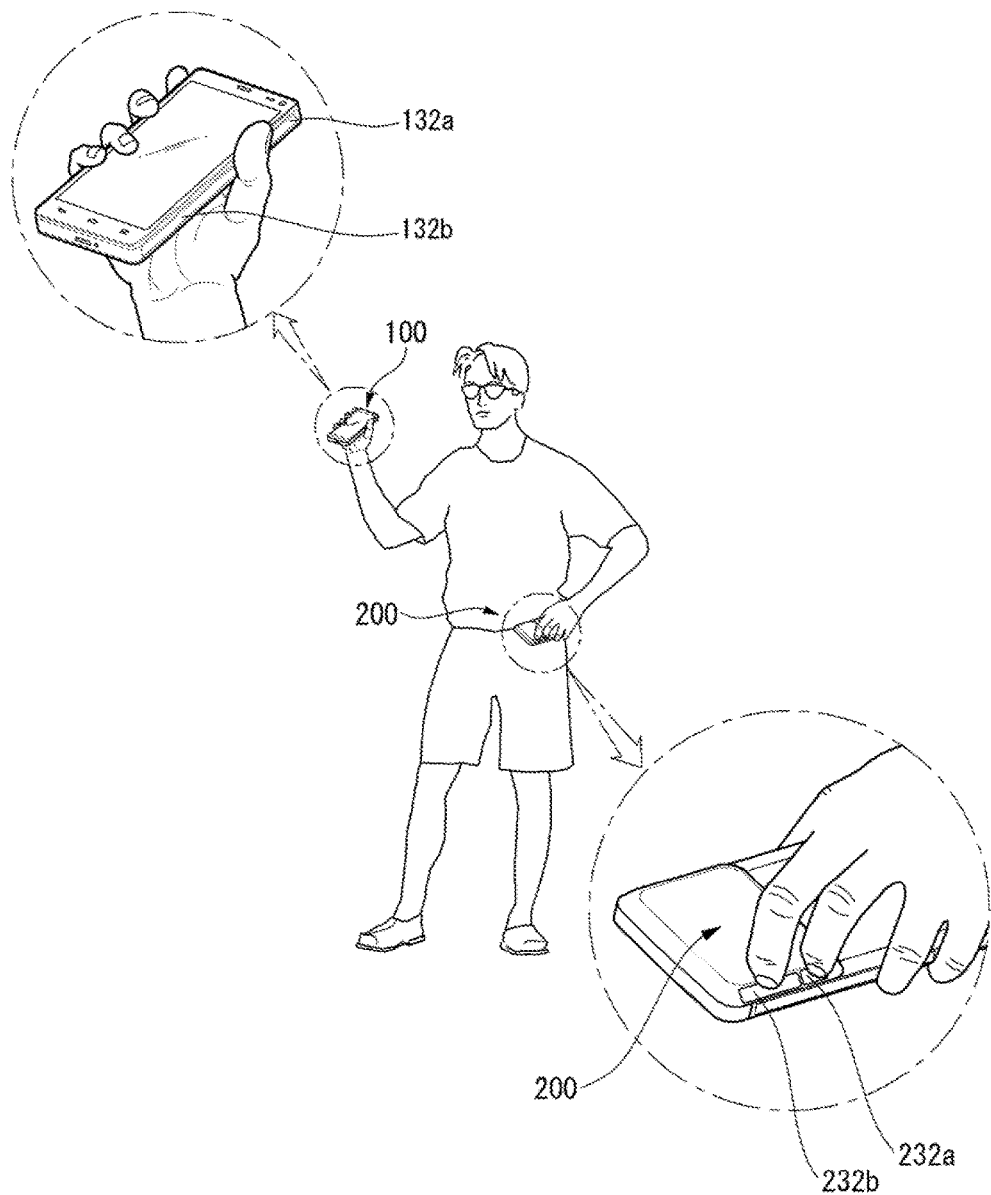

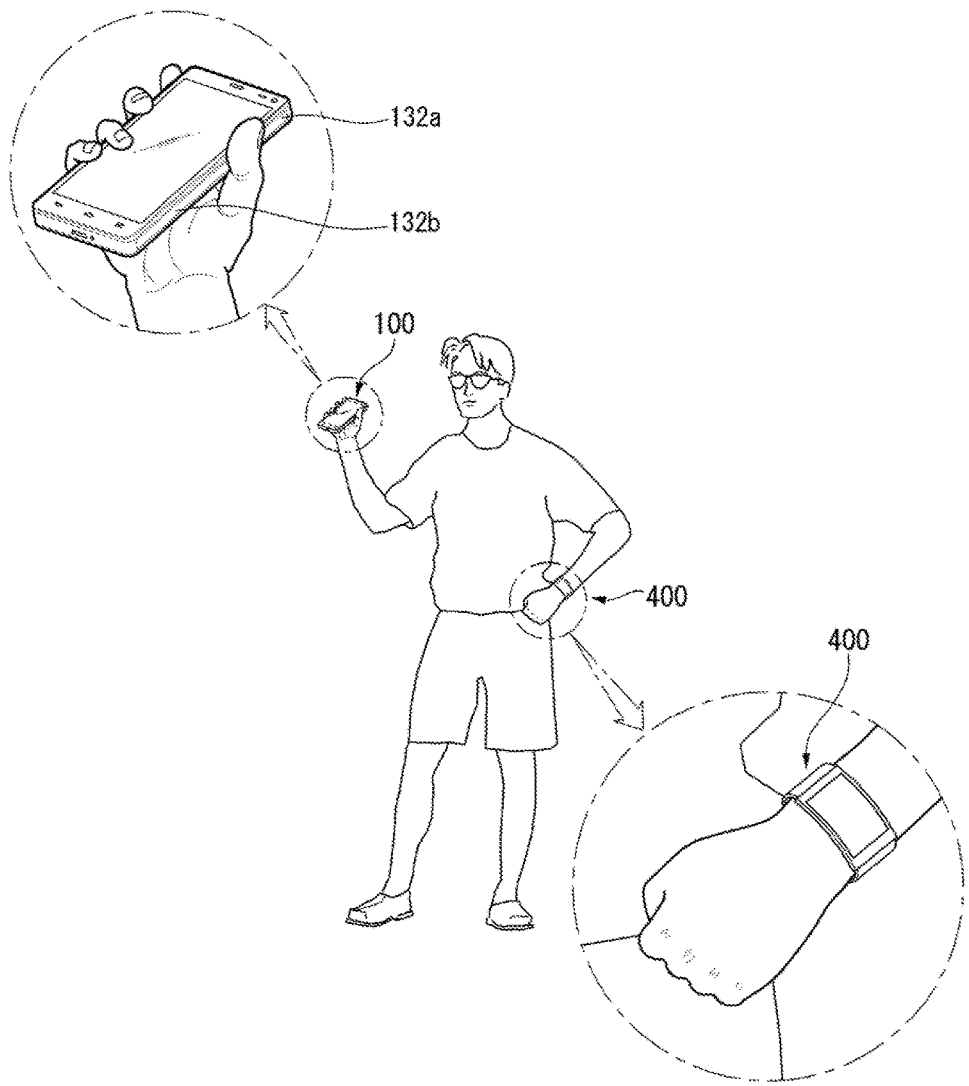
[Figure 6c]

【Figure 6d】
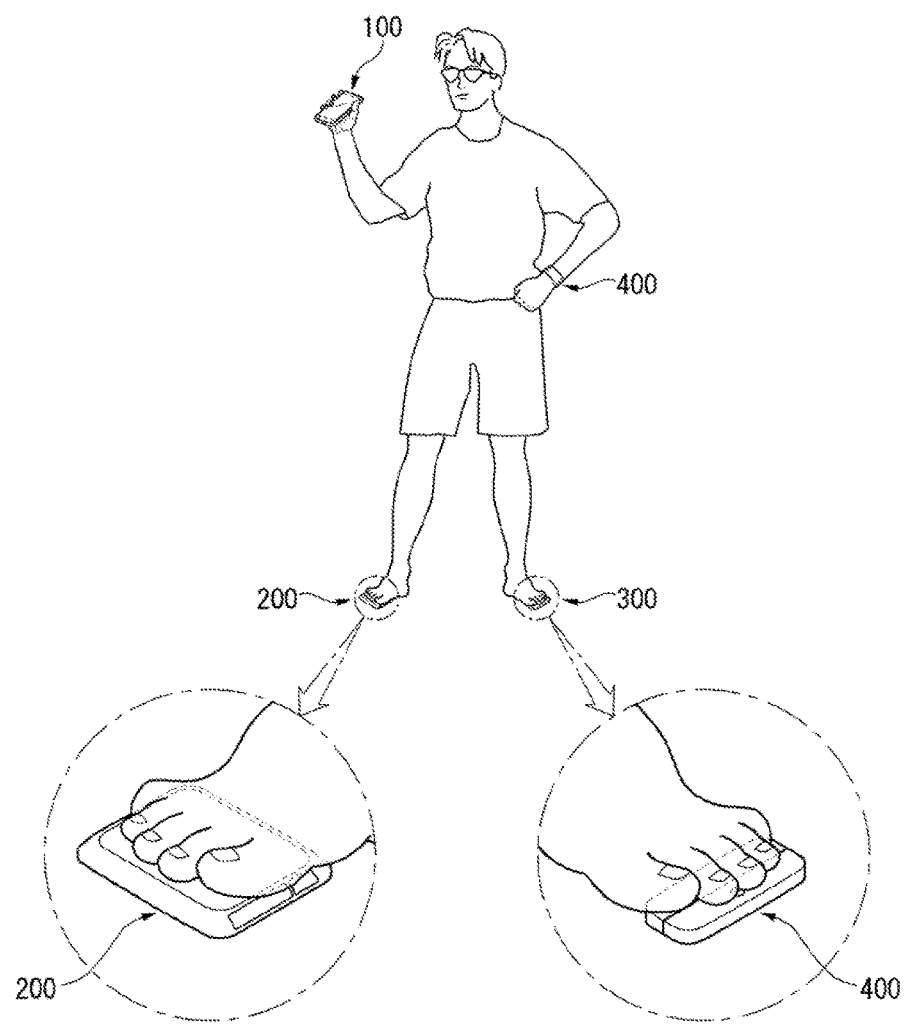

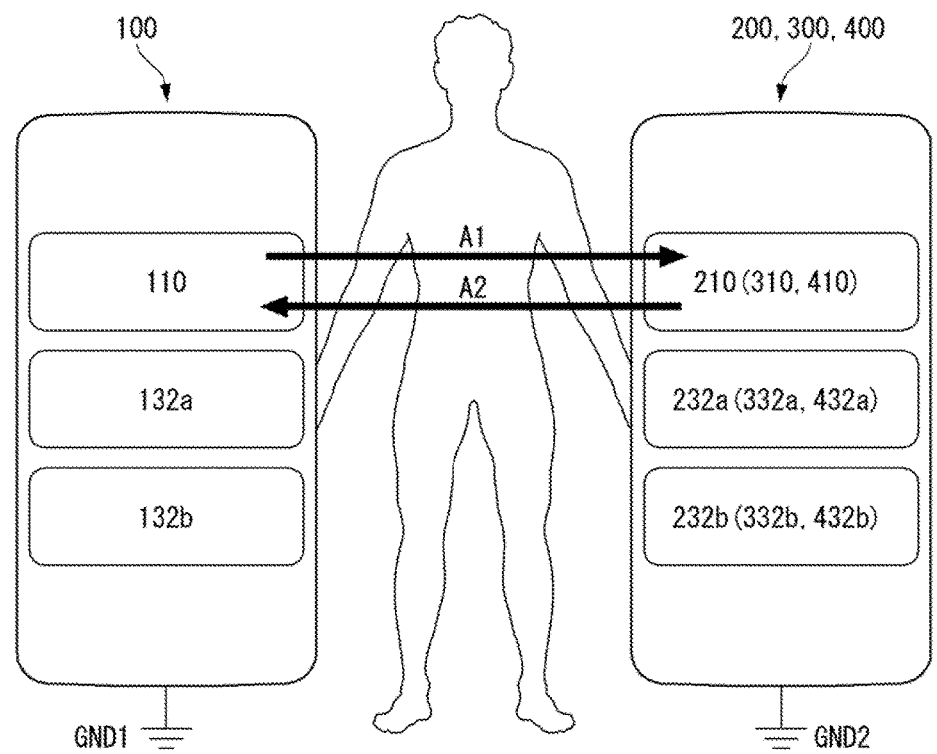
[Figure 7]

【Figure 8】
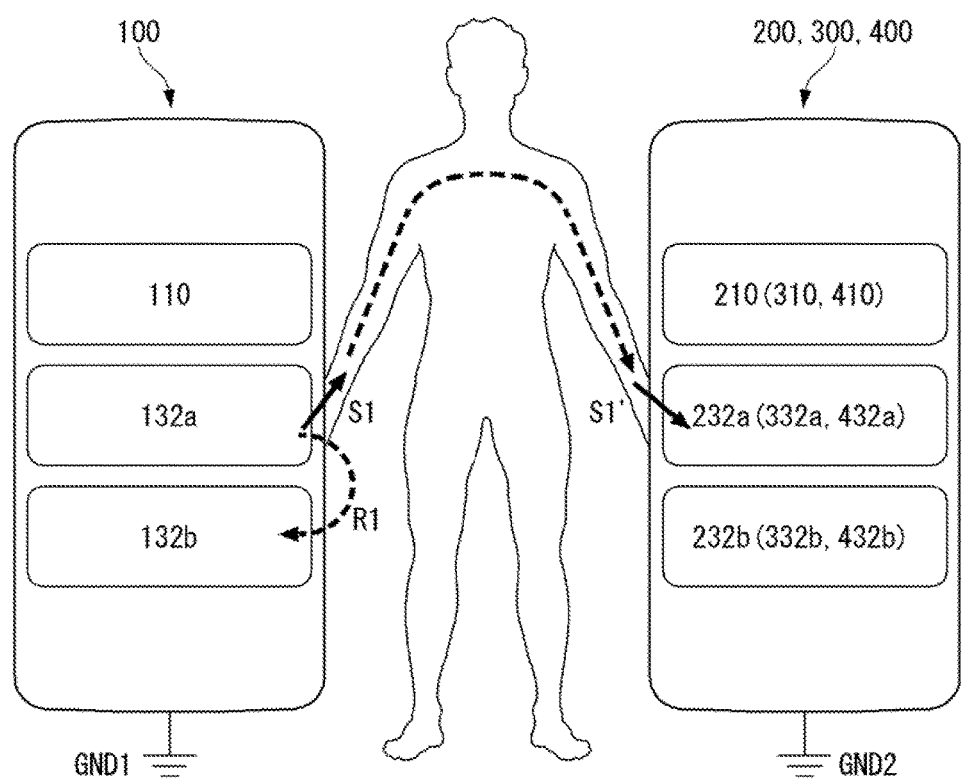

【Figure 9】
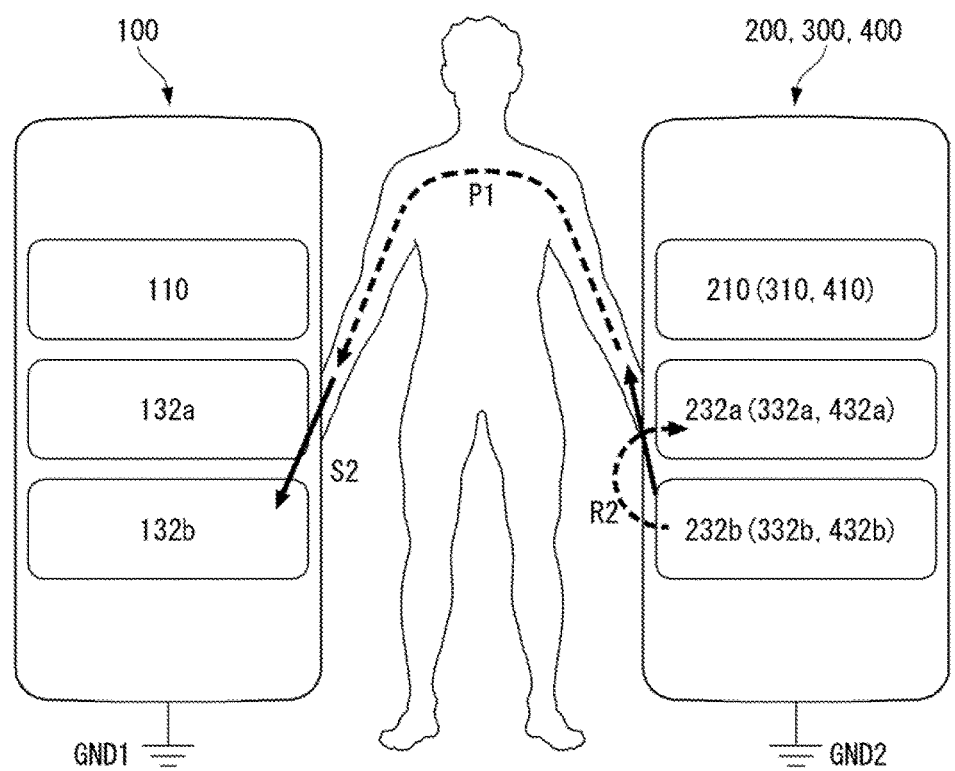

[Figure 10]
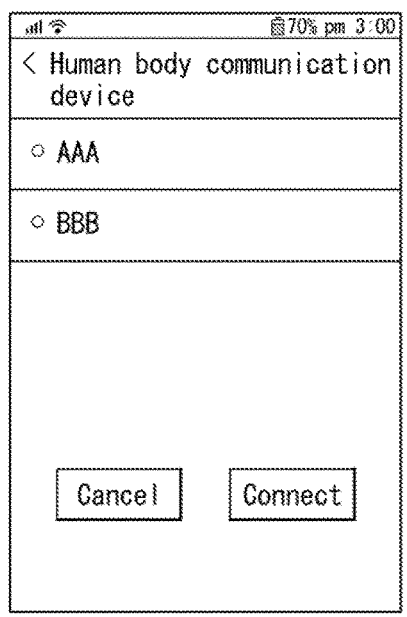
(a)
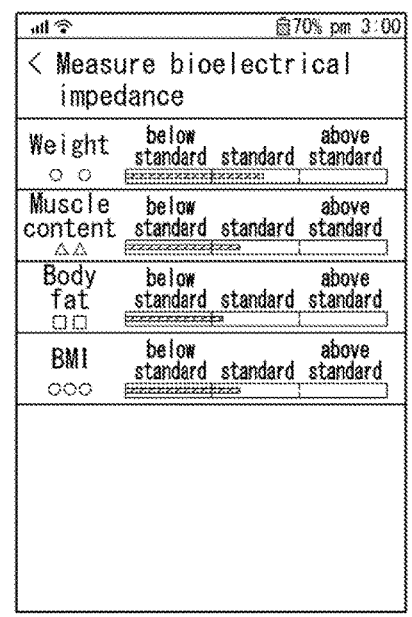
(b)

[Figure 11]
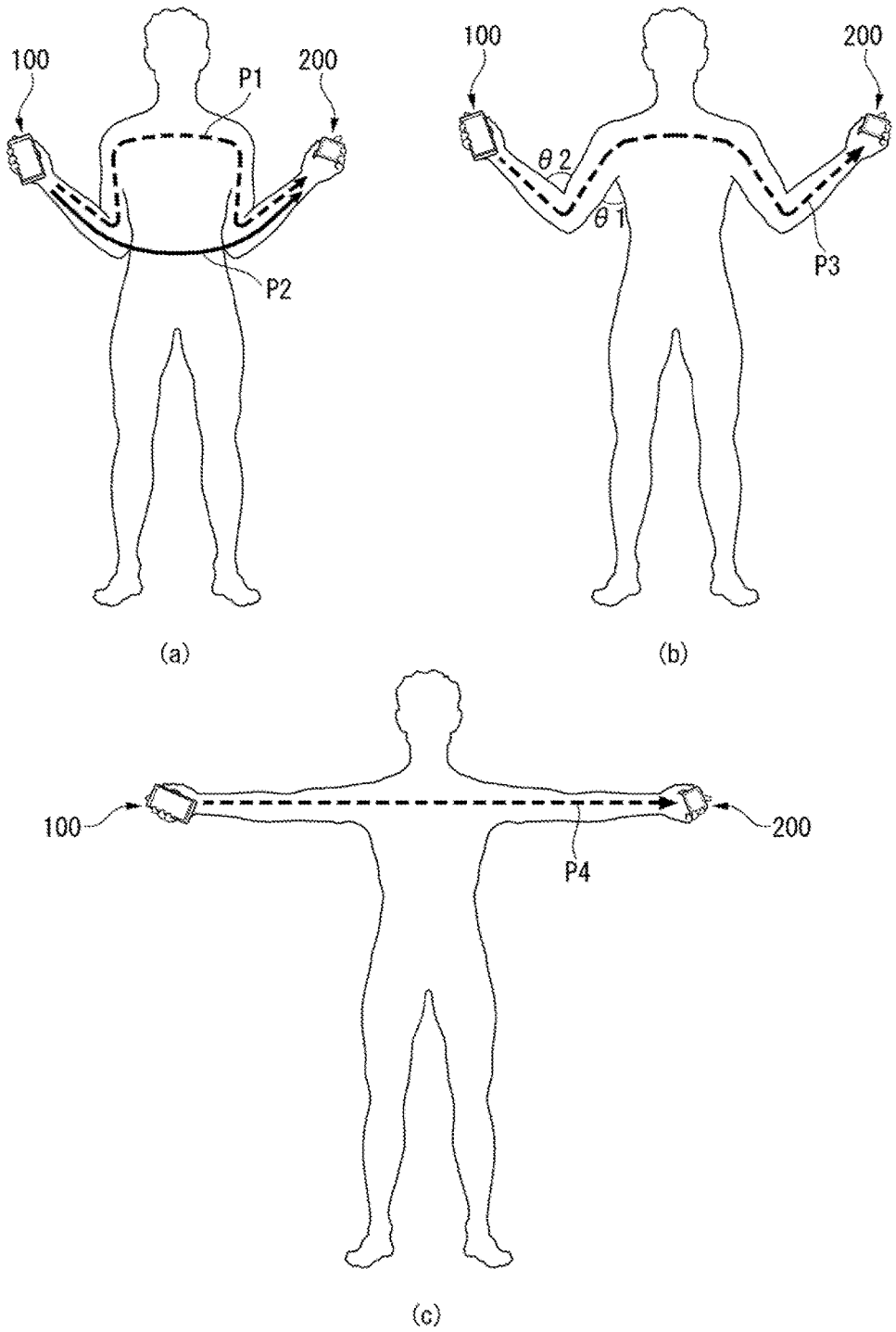

【Figure 12】
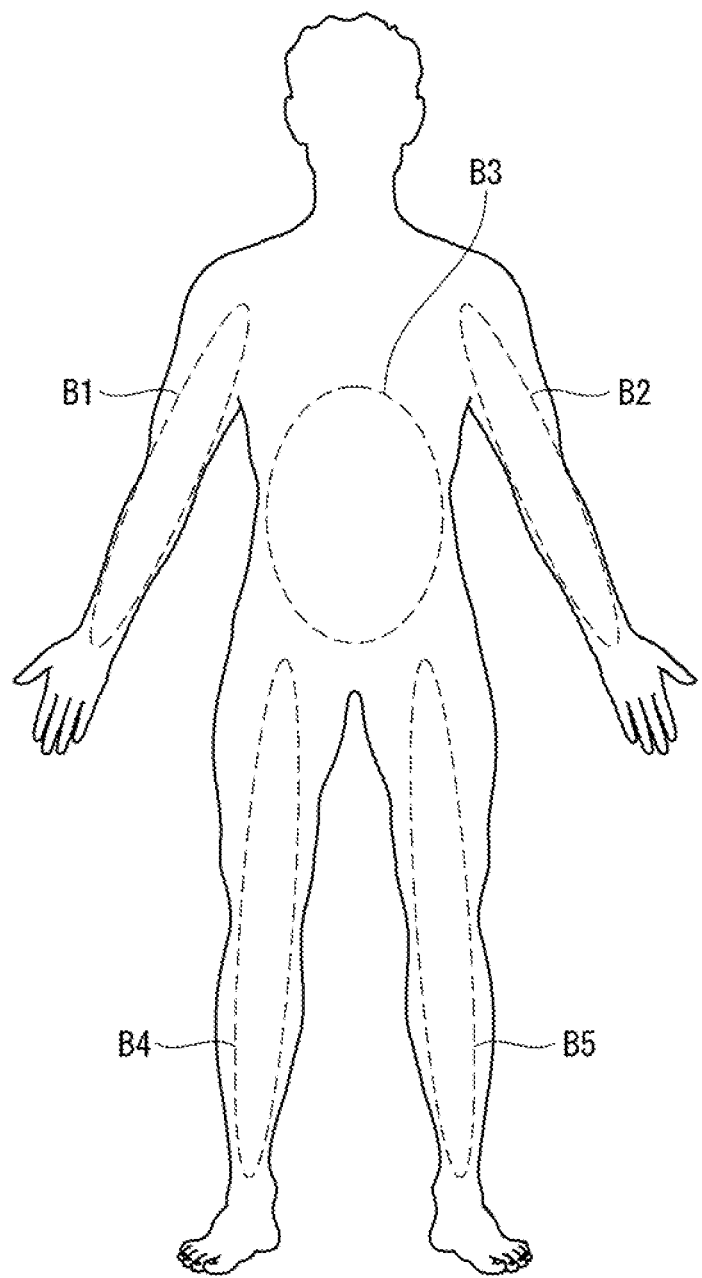

【Figure 13】
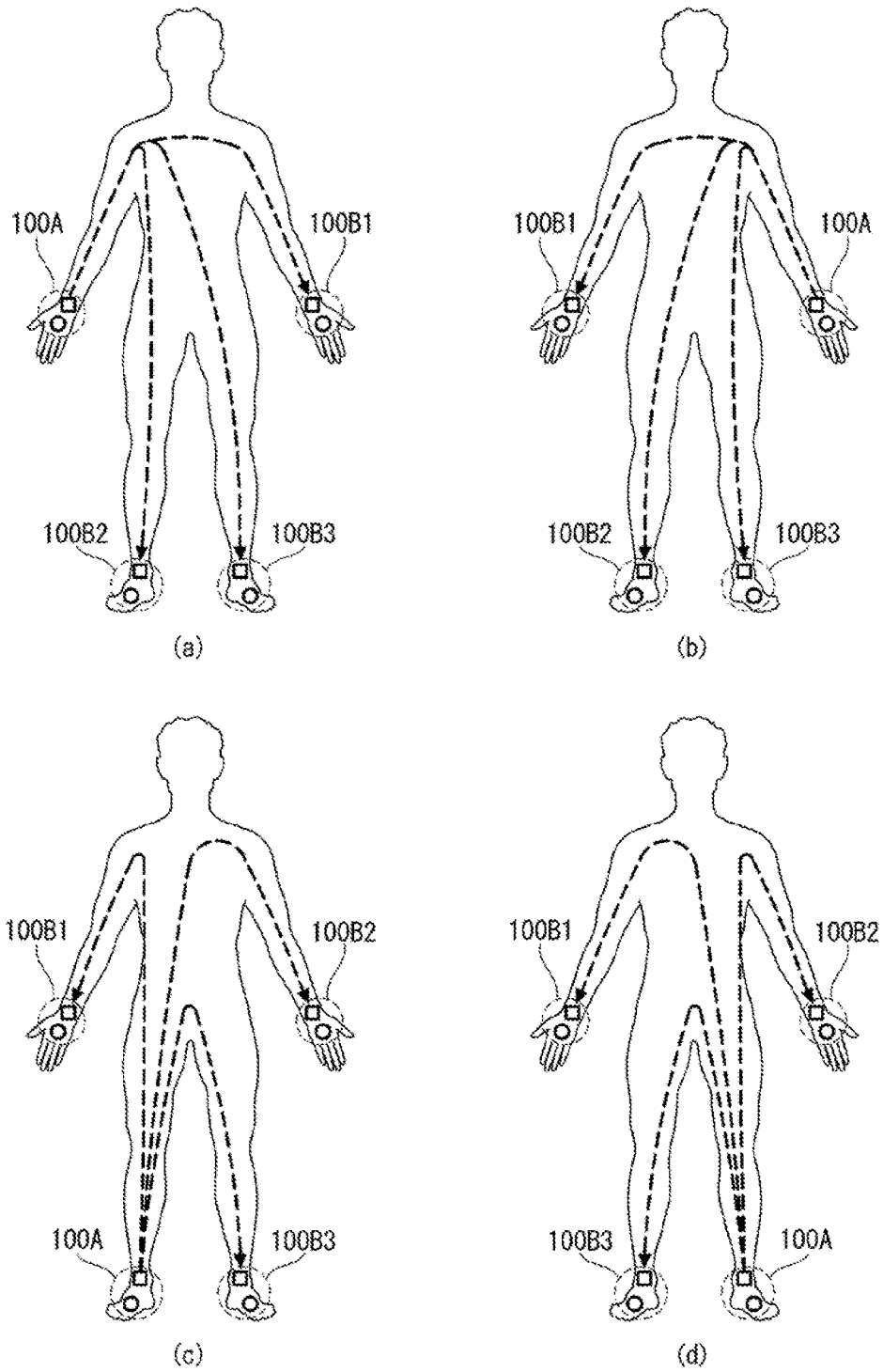

【Figure 14】
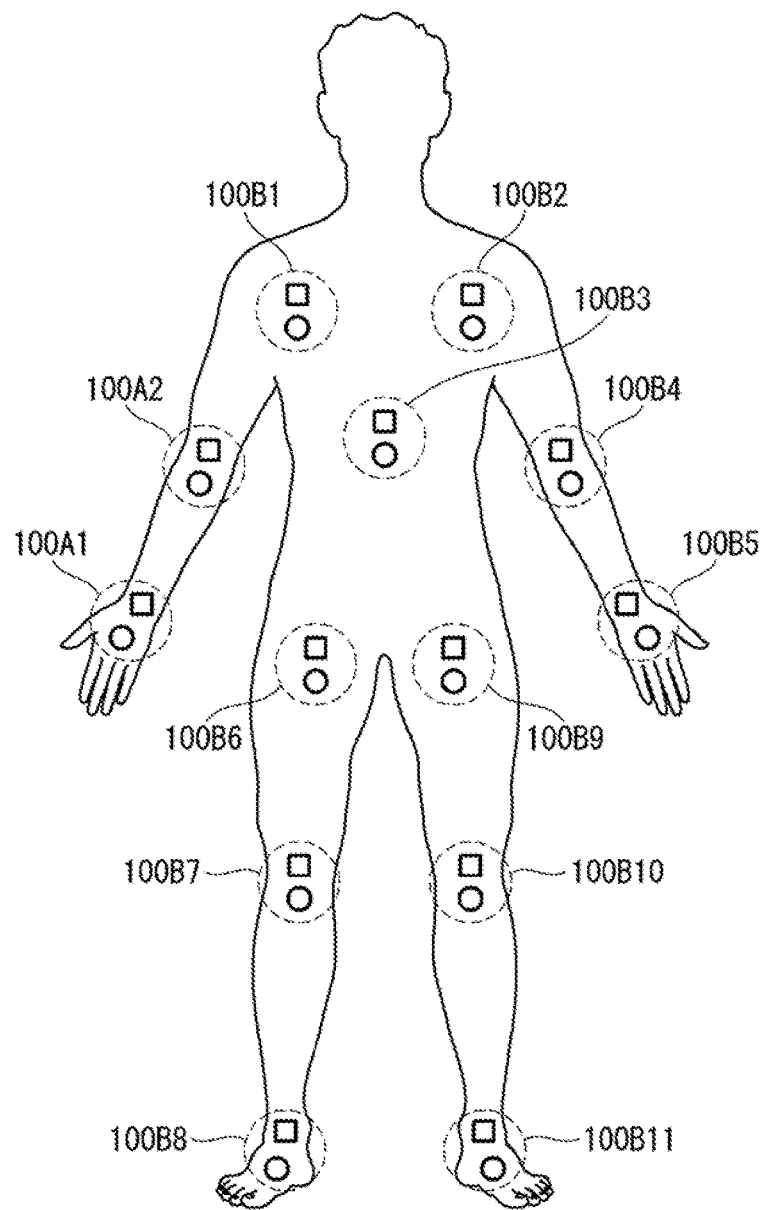

【Figure 15】
(a)
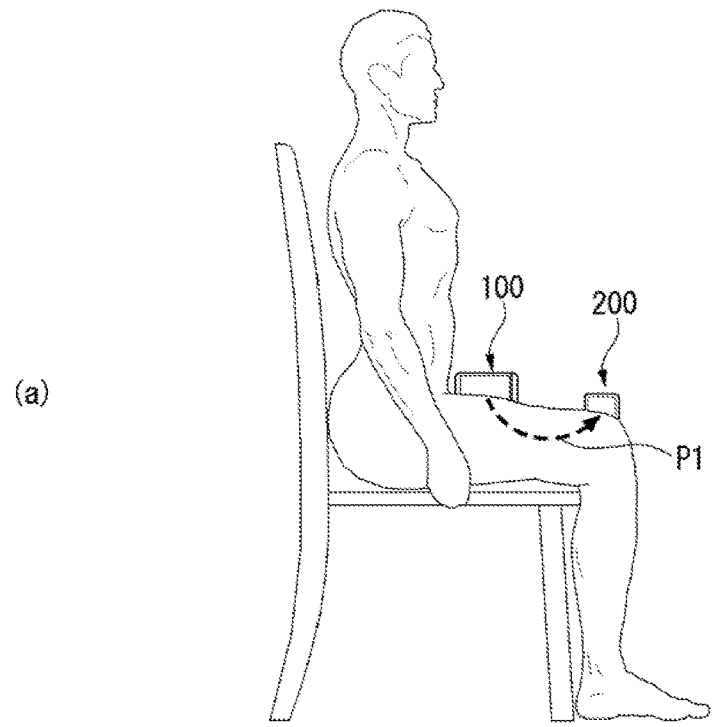
(b)
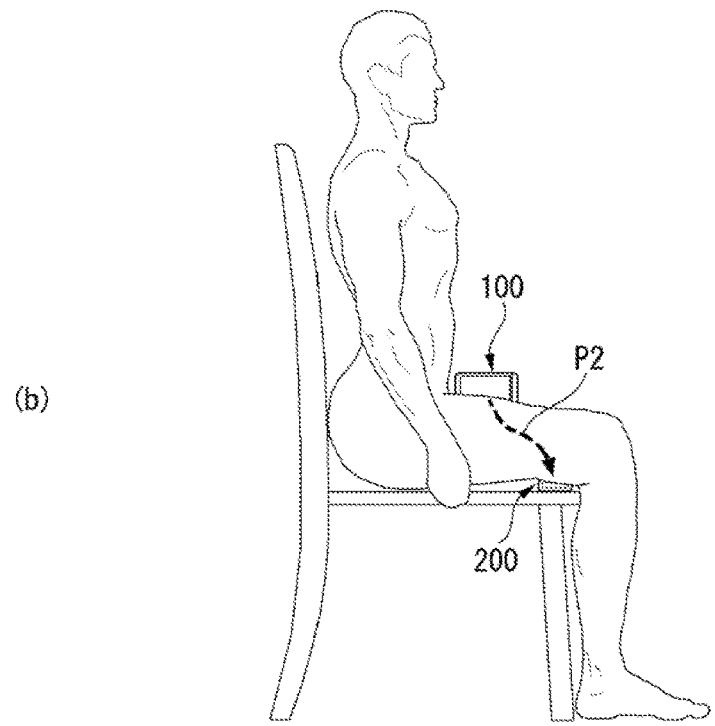

[Figure 16]
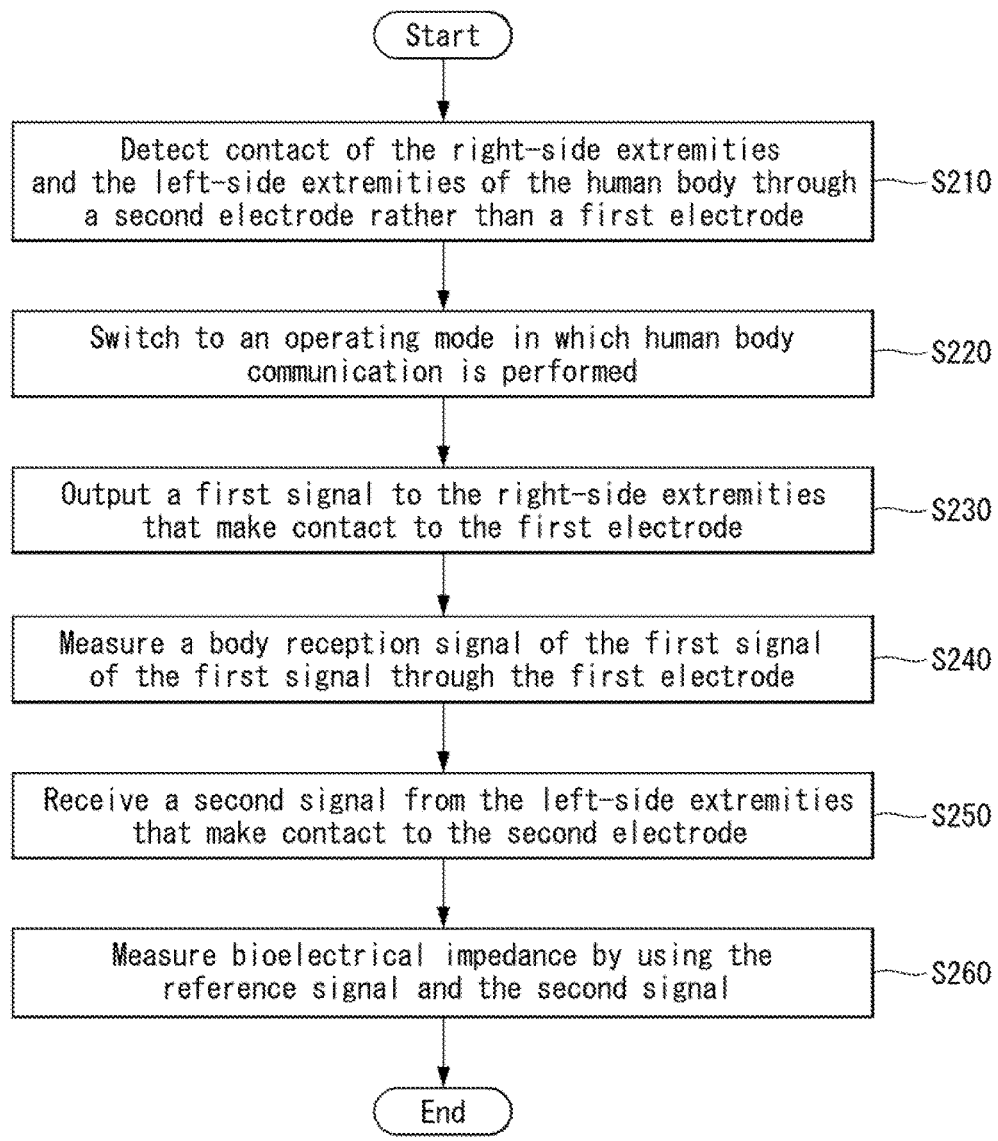

【Figure 17】
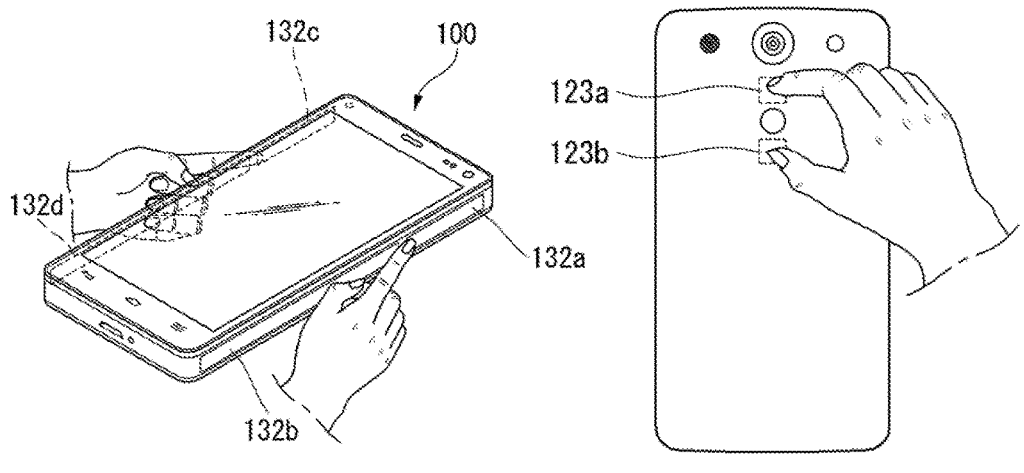
(a) (b)
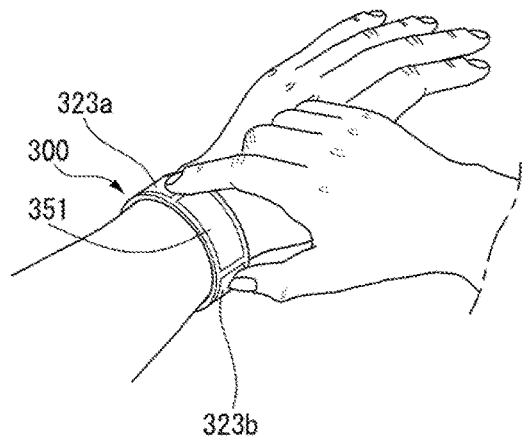
(c)

MOBILE TERMINAL AND METHOD OF CONTROLLING SAME

CROSS REFERENCE TO RELATED APPLICATIONS

This application is the National Phase of PCT International Application No. PCT/KR2016/010808, filed on Sep. 27, 2016, which claims priority under 35 U.S.C. 119(a) to Patent Application No. 10-2015-0141004, filed in Republic of Korea on Oct. 7, 2015, and Patent Application No. 10-2016-0123878, filed in Republic of Korea on Sep. 27, 2016, all of which are hereby expressly incorporated by reference into the present application.

TECHNICAL FIELD

The present invention relates to a mobile terminal providing a function of measuring bioelectric impedance and a method for controlling the terminal.

BACKGROUND ART

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such functions become more diversified, the mobile terminal can support more complicated functions such as capturing images or video, reproducing music or video files, playing games, receiving broadcast signals, and the like. By comprehensively and collectively implementing such functions, the mobile terminal may be embodied in the form of a multimedia player or device.

Efforts are ongoing to support and increase the functionality of mobile terminals. Such efforts include software and hardware improvements, as well as changes and improvements in the structural components.

Recently, mobile terminals are equipped with a plurality of sensors capable of measuring biometric signals, such as a temperature sensor and a heart rate measurement sensor, thereby measuring the health status of a user.

In particular, a mobile terminal is constructed with a plurality of constituting elements connected electrically to each other, and when the plurality of constituting elements are formed outside the mobile terminal, the mobile terminal may measure various types of biometric signals by using the elements.

DISCLOSURE

Technical Problem

Accordingly, an object of the present invention is to address the above-noted and other problems. Another object of the present invention is to provide a mobile terminal capable of controlling a current that uses a human body contacting two or more electrodes installed at each of different mobile terminals or a mobile terminal and a detachable electronic device as a current path to flow in bidirectional direction, thereby measuring a voltage difference by forming a common ground between different terminals or between a terminal and an electronic device and measuring bioelectric impedance by using the measured voltage difference; and a method for controlling the mobile terminal.

Another object of the present invention is to provide a mobile terminal capable of switching the function of two or more electrode units installed in the mobile terminal between a bioelectric impedance measurement mode and a mode for another function and measuring a voltage difference developed by a human body contacting two or more electrode units in the bioelectric impedance measurement mode, thereby enabling a user to measure bioelectric impedance; and a method for controlling the mobile terminal.

Technical Solution

To achieve the object and other objects, a mobile terminal according to one aspect of the present invention includes a body; a first and a second electrode installed respectively at least one side surface of the body and detecting contact of a first body area of a user; a wireless communication unit transmitting and receiving a first activation signal for human body communication to an external device in contact with a second body area; and a controller, when a first signal is output to the first body area through the first electrode, measuring a signal compensating for signal attenuation due to contact resistance between the first electrode and the first body area through the second electrode and setting the measured signal as a reference signal; and when a second signal, which has been generated at the external device and has passed through the user's body, is detected through the second electrode, measuring bioelectric impedance by using the reference signal and the second signal.

The second signal refers to a fourth signal generated at the external device and subsequently detected through the second electrode after passing through the user's body.

The fourth signal may refer to a signal generated from the first signal to have the same electric characteristics as those of a third signal which has passed through the user's body and has been detected by an electrode of the external device.

When the controller senses that the first body area actually makes contact with the first and the second electrode simultaneously, the controller may transmit the first activation signal to the external device through the wireless communication unit.

The first activation signal may include at least one of time, current, voltage, or frequency.

When receiving a second activation signal for the human body communication from the external device through the wireless communication unit, the controller may determine a master device by comparing the first activation signal with the second activation signal and when the mobile device is determined as the master device, transmit a signal which controls the mobile terminal to generate the fourth signal and output the generated fourth signal to the external device.

At least one of the first or the second body area is an extremity of a human body and may include at least one of arm or leg extremities.

The mobile terminal may further include an interface installed on one side surface of the body and attached to or detached from the external device, wherein the controller, when the external device is coupled through the interface, may be configured to function as a single device by the control of a master device.

The wireless communication unit may use one of Body Area Network (BAN), Bluetooth (BT), Bluetooth Low Energy (BLE), and WiFi communication method.

The mobile terminal may further include a sensing unit sensing a user's attitude related to a body part that grips the mobile terminal, wherein The controller may output guide information so that the user's attitude sensed through the sensing unit satisfies a predetermined criterion.

When a plurality of external devices are involved, the controller receives the second signal respectively from the plurality of external devices that make contact with the remaining body areas except for the second body area and measures a plurality of bioelectric impedance by using the reference signal and the plurality of second signals.

The plurality of bioelectric impedance may be provided as separate impedance developed between the first body area and the remaining body areas that make contact to the plurality of external devices.

Also, according to another aspect of the present invention, a mobile terminal includes a first electrode unit, a second electrode unit, and a controller, when contact to a first extremity area and a second extremity area of a human body is detected simultaneously through the first and the second electrode unit, switching to an operating mode for performing human body communication, outputting a first signal to the first extremity unit that makes contact to the first electrode unit, measuring a body reception signal of the first signal through the first electrode unit and setting up the measured the body reception signal as a reference signal, receiving a second signal from the second extremity area that makes contact to the second electrode unit, and measuring bioelectric impedance by using the reference signal and the second signal.

Technical Effects

The advantageous effects obtained by using a mobile terminal according to the present invention and a method for controlling the mobile terminal may be described as follows.

According to at least one of embodiments of the present invention, since a mobile terminal and a detachable electronic device are employed, a user may measure bioelectric impedance whenever and wherever needed by the user.

Also, according to at least one of embodiments of the present invention, since a conductive area formed on the surface of a mobile terminal may be used as an electrode for measuring bioelectric impedance without having to form a separate electrode for measuring bioelectric impedance in the mobile terminal or an electronic device attached to or detached from the mobile terminal, there is no need to secure a dedicated installation area.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

DESCRIPTION OF DRAWINGS

The present invention will become more fully understood from the detailed description given herein below and the accompanying drawings, which are given by illustration only, and thus are not limitative of the present invention, and wherein:

FIG. 1 is a block diagram of a mobile terminal in accordance with the present disclosure.

FIGS. 2a to 2d illustrate a mobile terminal according to the present invention and one example of a mobile terminal and a detachable electronic device seen from a different view direction.

FIG. 3a illustrates a concept of measuring bioelectric impedance through two devices separated from each other according to one embodiment of the present invention.

FIG. 3b illustrates one example of a block diagram implementing a function for measuring bioelectric impedance according to one embodiment of the present invention.

FIGS. 4 to 5 are flow diagrams illustrating a method for controlling a mobile terminal according to a first embodiment of the present invention.

FIGS. 6a to 6d illustrate use cases for measuring bioelectric impedance by using two different devices that make contact to different body areas according to a first embodiment of the present invention.

FIGS. 7 to 9 illustrate a signal flow for measuring bioelectric impedance according to a method for controlling a mobile terminal according to a first embodiment of the present invention.

FIG. 10 illustrates an example in which a bioelectric impedance measurement result is displayed according to a first embodiment of the present invention.

FIG. 11 illustrates an example of a user's attitude when bioelectric impedance is measured according to a first embodiment of the present invention.

FIGS. 12 to 15 illustrate a method for measuring bioelectric impedance of a particular body area by using two or more different electronic devices according to a first embodiment of the present invention.

FIG. 16 is a flow diagram illustrating a method for controlling a mobile terminal according to a second embodiment of the present invention.

FIG. 17 illustrates a method for controlling a mobile terminal according to a second embodiment of the present invention.

BEST MODE FOR INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

FIG. 1 is a block diagram of a mobile terminal in accordance with the present disclosure.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least part of the constituting elements may operate in collaboration with each other to implement an operation or control of a mobile terminal or a method for controlling the mobile terminal according to various embodiments described below. Also, the operation or control of the mobile terminal or the method for controlling a mobile terminal may be implemented in the mobile terminal by at least one application program stored in the memory 170.

Referring still to FIG. 1, various components depicted in this figure will now be described in more detail.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA(High Speed Uplink Packet Access), Long Term Evolution (LTE), LTE-A(Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB(Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal. As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 100. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches include a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 2a to 2d, the mobile terminal 100 is described with reference to a bar-type terminal body.

However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

Here, the terminal body may be understood as a concept referring to the mobile terminal 100 as at least one aggregate body.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

At least two electrodes 134a, 134b may be installed on the side surface of the rear case 102 of the mobile terminal 100. At this time, at least two electrodes 134a, 134b installed on the side surface of the rear case 102 may form conductive areas including an antenna pattern. The at least two electrodes 134a, 134b may perform the function of an antenna for most cases and switch the function to be used for human body communication only when a human body makes contact with the at least two electrodes 134a, 134b simultaneously.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal includes a display unit 151, a first and a second audio output modules 151a/151b, a proximity sensor 141, an illumination sensor 142, an optical output module 154, a first and a second cameras 121a/121b, a first and a second manipulation units 123a/123b, a microphone 122, interface unit 160 and the like.

It will be described for the mobile terminal as shown in FIGS. 2a and 2b. The display unit 151, the first audio output module 151a, the proximity sensor 141, an illumination sensor 142, the optical output module 154, the first camera 121a and the first manipulation unit 123a are arranged in front surface of the terminal body, the second manipulation unit 123b, the microphone 122 and interface unit 160 are arranged in side surface of the terminal body, and the second audio output modules 151b and the second camera 121b are arranged in rear surface of the terminal body.

However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. For example, the display unit 151 may display information of an execution screen of an application program run on the mobile terminal 100 or information of a User Interface (UI) or Graphic User Interface (GUI) according to the execution screen information.

The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a receiver delivering voice to the ear of a user, and the second audio output unit 152b may be implemented in the form of a loud speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 2b illustrates the first manipulation unit 123a as a touch key, but possible alternatives include a mechanical key, a push key, a touch key, and combinations thereof. In other words, when pressure larger than a preset value is applied to the first and the second manipulation unit 123a, 123b, the first and the second manipulation unit 123a, 123b may be used as a push key to deliver the pressure to the dome key D1, D2 formed in the lower part. On the other hand, when pressure smaller than a preset value is applied to the first and the second manipulation unit 123a, 123b, the first and the second operation unit 123a, 123b may be used as a touch key.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

Also, the first and the second manipulation unit 123a, 123b may be composed of two or more electrodes 123aa, 123ab, 123ba, 123bb, respectively and may activate human body communication when contact of a human body to all of two or more electrodes 123aa, 123ab, 123ba, 123bb is detected.

As another example of the user input unit 123, a rear input unit (123a, 123b, P) may be located on the rear surface of the terminal body. The rear input unit (123a, 123b, P) can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit (123a, 123b, P) may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit (123*a*, 123*b*, P) can be positioned at most any location of the rear side of the terminal body.

Embodiments that include the rear input unit (123*a*, 123*b*, P) may implement some or all of the functionality of the first manipulation unit 123*a* in the rear input unit. As such, in situations where the first manipulation unit 123*a* is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121*b* is shown located at the rear side of the terminal body and includes an image capturing direction that is substantially opposite to the image capturing direction of the first camera unit 121*a*. If desired, second camera 121*a* may alternatively be located at other locations, or made to be moveable, in order to have a different image capturing direction from that which is shown.

The second camera 121*b* can include a plurality of lenses arranged along at least one line. The plurality of lenses may also be arranged in a matrix configuration. The cameras may be referred to as an "array camera." When the second camera 121*b* is implemented as an array camera, images may be captured in various manners using the plurality of lenses and images with better qualities.

As shown in FIG. 1C, a flash 124 is shown adjacent to the second camera 121*b*. When an image of a subject is captured with the camera 121*b*, the flash 124 may illuminate the subject.

As shown in FIG. 1B, the second audio output module 152*b* can be located on the terminal body. The second audio output module 152*b* may implement stereophonic sound functions in conjunction with the first audio output module 152*a*, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body.

The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

As described with reference to FIG. 1, a mobile terminal according to the present invention may employ short range communication technologies such as Bluetooth™, Radio Frequency Identification (RFID), Infrared Data Association (IrDA), Ultra Wideband (UWB), ZigBee, Near Field Communication (NFC), and Wireless Universal Serial Bus (USB).

Among these, an NFC module installed in a mobile terminal supports non-contact type short range wireless communication between terminals within a distance of 10 cm more or less. An NFC module may operate in one of a card mode, reader mode, and P2P mode. In order to operate an NFC module in the card mode, the mobile terminal 100 may further include a security module storing card information. At this time, a security module may refer to a physical medium such as a Universal Integrated Circuit Card (UICC) (for example, Subscriber Identification Module (SIM) or Universal SIM (USIM)), secure micro SD, and sticker or a logical medium embedded in a mobile terminal (for example, an embedded Secure Element (SE)). Data may be exchanged between an NFC module and a security module.

If an NFC module is operated in the card mode, a mobile terminal may deliver card information stored therein in a similar way as stored in a conventional IC card to the outside. More specifically, if a mobile terminal storing card information of a payment card such as a credit card or a bus card is put close to a payment terminal, mobile short range payment may be processed while, if a mobile terminal storing card information of an access card is put close to an access terminal, an approval procedure for the access may be initiated. Those cards such as credit cards, transportation cards, and access cards may be installed in the security module in the form of an applet, and the security module may store card information about the installed card. Here, card information of a payment card may include at least one of a card number, amount of balance, and use details; and the card information of an access card may include at least one of the name of a user, number (for example, student number), and access records.

If an NFC module is operated in the reader mode, a mobile terminal may read out data from an external tag. At this time, the data that a mobile terminal receives may be coded according to the NFC data exchange format defined by the NFC forum. The NFC forum specifies four record types. More specifically, the NFC forum specifies four Record Type Definitions (RTDs): smart poster, text, Uniform Resource Identifier (URI), and general control. When data received from a tag corresponds to the smart poster type, the controller executes a browser (for example, Internet browser) while, when data received from a tag corresponds to the text type, the controller may execute a text viewer. When data received from a tag corresponds to the URI type, the controller may execute a browser or makes a phone call; when data received from a tag corresponds to the general control type, the controller may execute an appropriate operation according to the content of the control.

If an NFC module is operated in the Peer-to-Peer (P2P) mode, a mobile terminal may perform P2P communication with other mobile terminal. At this time, P2P communication may employ Logical Link Control Protocol (LLCP). A connection may be established between a mobile terminal and other mobile terminal for P2P communication. At this time, the established connection may be classified as a connectionless mode in which a connection is terminated after one packet is exchanged or a connection-oriented mode in which packets are exchanged continuously. Through P2P communication, data such as electronic name cards, contact information, digital photos, and URL and setup parameters for Bluetooth and Wi-Fi connections may be exchanged. However, since a valid distance of NFC communication is short, the P2P mode may be employed effectively for exchanging a small amount of data.

Referring to FIGS. 2c and 2d, the disclosed mobile terminal 100 may be equipped with the camera module 200 or the audio module 300 in a detachable structure. In other words, part of a body frame of the mobile terminal may be formed so that it may be inserted into another frame, or an electronic device may be fastened to the body of the mobile terminal.

More specifically, a battery 191 may be inserted or removed by separating the lower frame of the body of the mobile terminal from the upper frame of the body. Since at least one surface of the camera module 200 and the audio module 300 is constructed to have a frame in the same form of the lower frame of the body of the mobile terminal, the camera module 200 and the audio module 300 may form a detachable structure and capable of replacing the lower frame of the mobile terminal. At this time, the battery 191 may be combined with the lower frame part formed in the camera module 200 or the audio module 300 so that it may be inserted into the upper frame of the mobile terminal 100.

Two electrodes 232a, 232b may be formed on at least one surface of the camera module 200. In the same way, two electrodes 332a, 332b may be formed on at least one surface of the audio module 300. At this time, the two electrodes 232a, 232b, 332a, 332b have to be formed on the surface exposed to the outside respectively after the camera module 200 and the audio module 300 are combined with the mobile terminal 100. When the camera module 200 or the audio module 300 not in use, another frame may be inserted onto the lower frame so that the mobile terminal may be put into dust-proof condition.

When the camera module 200 and the audio module 300 are combined with the mobile terminal 100, they may operate as a single device according to the control of the controller 180 of the mobile terminal 100. Also, when the camera module 200 and the audio module 200 are separated from the mobile terminal 100, they may function as a separate electronic device or function as an auxiliary device being coupled with the mobile terminal 100.

In what follows, embodiments related to a control method that may be implemented in the mobile terminal as constructed above will be described with reference to appended drawings. It should be clearly understood by those skilled in the art that the present invention may be embodied in other specific forms without departing from the technical spirit and essential characteristics of the present invention.

FIG. 3a illustrates a concept of measuring bioelectric impedance through two devices separated from each other according to one embodiment of the present invention.

Referring to FIG. 3a, according to one embodiment of the present invention, Bioelectrical Impedance Analysis (BIA) is measured by using two electronic devices physically separated from each other. In what follows, the BIA may be called bioelectric impedance. Also, the two electronic devices may be called a first mobile terminal 100A and a second mobile terminal 100B, respectively.

The first mobile terminal 100A and the second mobile terminal 100B may make contact to body areas of a user while they are physically separated from each other. Meanwhile, if a first body area of a user makes contact to an electrode of the first mobile terminal 100A and a second body area makes contact to an electrode of the second mobile terminal 100B, since the two mobile terminals are physically separated from each other, it may be understood that the first mobile terminal 100A and the second mobile terminal 100B have grounds GND1, GND2 actually different from each other.

When a first body area (for example, one finger of the left arm) of a user makes contact to an electrode of the first mobile terminal 100A and a second body area (for example, one finger of the right arm) of the user makes contact to an electrode of the second mobile terminal 100B, the first mobile terminal 100A may generate a predetermined test signal. The test signal may be output to the first body area and delivered to the second mobile terminal 100B through the second body area by using the human body of the user as a mediator material.

The second mobile terminal 100B may generate a feedback signal corresponding to a predetermined test signal delivered through the human body. The feedback signal may be generated on the basis of electrical characteristics of the test signal delivered through the human body.

Here, the test signal generated and delivered by the first mobile terminal 100A may experience a predetermined amount of first attenuation due to contact resistance of the first body area and may further experience second attenuation as the test signal goes through the human body while the first attenuation is being made on the test signal. Therefore, a signal received by the second mobile terminal 100B may correspond to the test signal after a predetermined attenuation process (the first attenuation and the second attenuation) has been made thereupon. The second mobile terminal 100B may generate a feedback signal having the same electrical characteristics of the test signal after the attenuation process has been made thereupon.

When the second mobile terminal 100B generates the feedback signal and outputs the generated feedback signal to the second body area, the feedback signal undergoes a predetermined attenuation process in the same way as described above and is delivered to the first mobile terminal 100A through the first body area.

The first mobile terminal 100A may measure bioelectric impedance of the user on the basis of electrical characteristics of the test signal delivered to the second mobile terminal 100B and the feedback signal received from the second mobile terminal 100B.

In what follows, a flow of a signal transmitted and received through the human body as a mediator material between the first mobile terminal 100A and the second mobile terminal 100B will be described in more detail.

The first mobile terminal 100A and the second mobile terminal 100B may be equipped with a TX electrode and an RX electrode, respectively. The first mobile terminal 100A may be equipped with a first TX electrode and a first RX electrode. The second mobile terminal 100B may be equipped with a second TX electrode and a second RX electrode. Also, the first mobile terminal 100A may be further equipped with a predetermined IC chip ($IC_A$) capable of processing a signal transmitted and received through the first TX electrode and the first RX electrode for measuring bioelectric impedance. The IC chip may be integrated with the controller of a mobile terminal or installed separately from the controller. Meanwhile, the second mobile terminal 100B may also be equipped with an IC chip ($IC_B$) performing the same function as described above.

The first mobile terminal 100A may output a first signal (S1, a test signal) to a first body area which makes contact to the first TX electrode. The first signal S1 is delivered to the second mobile terminal 100B through a second body area making contact to the second RX electrode by using the human body of the user connected to the first body area as a mediator material. At this time, a signal detected by the second mobile terminal 100B through the second TX electrode is a third signal S1' obtained from the first signal S1 after a predetermined amount of attention has been made thereupon.

The second mobile terminal 100B generates a fourth signal P1 on the basis of the electrical characteristics of the third signal S1'. The electrical characteristics may include current, voltage, frequency, and amplitude characteristics, and in one example, the electrical characteristics of the fourth signal P1 may have the same electrical characteristics of the third signal S1'.

The second mobile terminal 100B outputs the generated fourth signal P1 through a second TX electrode to a second body area which makes contact to the second TX electrode, where the fourth signal P1 is delivered to the first RX electrode by using the user's body connected to the second body area as a mediator material. The fourth signal P1 is detected at the first RX electrode as a second signal S2 which has been undergone a predetermined amount of attenuation while flowing through the human body.

The first mobile terminal 100A measures bioelectric impedance by using the first signal S1 and the second signal S2. More specifically, when the first signal S1 is output to the first body area which makes contact to the first TX electrode, the first mobile terminal 100A measures bioelectric impedance by using a reference signal, which takes into account an amount of attenuation made due to skin contact resistance between the first TX electrode and the first body area, and the second signal S2.

Here, the first signal S1, the second signal S2, the third signal S1', the fourth signal P1, and the reference signal may be defined as follows (it is assumed that the first mobile terminal 100A is a master device, and a second mobile device 100B is a slave device).

The first signal S1 is generated by a test signal generator of the first mobile terminal 100A to measure bioelectric impedance and is output to the second mobile terminal 100B.

The reference signal is obtained from the first signal S1 as a portion thereof actually delivered to the first body area by taking into account the skin contact resistance developed against the first body area which makes contact to the first TX electrode. For example, the reference signal may correspond to an actual current value of a signal injected into the user's body. The reference signal is used directly for calculating bioelectric impedance.

The third signal S1' is obtained from the first signal S1 as it passes through the user's body and is detected at the second RX electrode of the second mobile terminal.

The fourth signal P1 is a signal generated by the test signal generator of the second mobile terminal 10B to have the same electrical characteristics of the third signal S1'.

Meanwhile, the first mobile terminal 100A and the second mobile terminal 100B may perform human body communication through a Body Area Network (BAN).

In the description above, signal generation and flow has been described under the assumption that the first mobile terminal 100A is a master device and the second mobile terminal 100B is a slave device. However, the present invention is not limited to the specific assumption. In other words, the first mobile terminal 100A and the second mobile terminal 100B may be equipped with an IC chip for measuring bioelectric impedance by using a signal transmitted and received through an appropriate electrode for performing human body communication and through the human body communication. Therefore, if either of the mobile terminals is determined as a master device, the other one is assigned as a slave device to perform human body communication.

FIG. 3b illustrates one example of a block diagram implementing a function for measuring bioelectric impedance according to one embodiment of the present invention.

Referring to FIG. 3b, the first mobile terminal 100A and the second mobile terminal 100B may be equipped with a chip which implements a function of measuring bioelectric impedance. In what follows, descriptions are given with respect to the $IC_A$ chip installed in the first mobile terminal 100A.

The bioelectric impedance measurement module $IC_A$ may include a test signal generator 1001, comparator 1003, and BIA measurement module 1005.

The bioelectric impedance measurement module $IC_A$ may perform human body medium communication with the second mobile terminal 100B through a first TX electrode and a first RX electrode.

The test signal generator 1001 may generate a test signal having a predetermined voltage, current, and amplitude when the first mobile terminal 100A is a master device. Meanwhile, when the first mobile terminal 100A is a slave device, the test signal generator 1001 may generate a feedback signal on the basis of a test signal received from a master device.

The comparator 1003 compares a signal output from each terminal and a received signal. For example, the comparator of the second mobile terminal 100B compares a first signal S1 output from the first mobile terminal 100A with a third signal S1', which is the first signal S1 detected by the second mobile terminal 100B after the first signal S1 passes through a human body, and determines an average amount of attenuation due to a human body. If the third signal S1' is determined to reveal a difference from the first signal S1 beyond a predetermined reference range, the controller of the second mobile terminal 100B determines that an attenuation effect due to the human body exceeds the reference range and an abnormality exists in a bioelectrical signal.

When it is determined from comparison of two signals performed by the comparator that a difference between the two signals lies within the predetermined reference range, the controller of the second mobile terminal 100B may control the test signal generator to generate a feedback signal.

Meanwhile, the comparator may compare the reference signal with the second signal S2, which is obtained from a feedback signal generated by the second mobile terminal 100B as the feedback signal passes through the user's body and is detected through the first RX electrode of the first mobile terminal 100A.

The BIA measurement module 1005 measures bioelectric impedance by using the reference signal and the second signal on the basis of the aforementioned comparison result of the comparator. In other words, even though the current of the reference signal is the same as the current of the second signal, there is a difference between the voltage of the reference signal and the voltage of the second signal. Therefore, bioelectric impedance may be calculated by using the voltage difference between the reference signal and the second signal; and the current of the reference signal (current of the second signal).

FIGS. 4 to 5 are flow diagrams illustrating a method for controlling a mobile terminal according to a first embodiment of the present invention.

According to a first embodiment of the present invention, bioelectric impedance may be measured by using two different mobile terminals or by using a mobile terminal and a detachable electronic device. At this time, two different mobile terminals may be chosen from a handheld phone, a watch phone, or a wearable electronic device such as a glass-type mobile terminal. Also, a detachable electronic device may be a camera module or an audio module that may be physically combined with a mobile terminal. It is assumed that two different mobile terminals and a mobile terminal and a detachable electronic device have two or more electrodes respectively.

Referring to FIG. 4, when detecting a body contact through a first and a second electrode formed on a mobile terminal S110, the controller 180 of a mobile terminal detects an external electronic device capable of performing human body communication S120 and transmits a human body communication activation signal to the external electronic device S130. Here, the external electronic device may be another mobile terminal, module detachable from a mobile terminal, watch coupled to a mobile terminal, or glass coupled to a mobile terminal.

The controller 180 may detect contact to a first extremity or a second extremity of a human body through a first and a second electrode. At this time, by outputting or receiving a particular signal, the controller 180 may check whether an extremity in the same direction has been detected at the first and the second electrode. Here, a first extremity and a second extremity may represent extremities in the left part of the body and extremities in the right part of the body or separated extremities of the body. For example, a first extremity may represent a right finger, and a second extremity may represent a left finger.

When human body communication is activated, the controller 180 may detect an external electronic device capable of performing human body communication. More specifically, the controller 180 may detect an electronic device that makes contact to the human body at the opposite of the first electrode and the second electrode. Also, through a short range communication method, the controller 180 may detect another external electronic device which has been activated for human body communication.

Human body communication or human skin communication refers to the technology that connects a wearable or implantable-type sensor or a device wirelessly and uses the human body as a communication medium.

The controller may transmit a human body communication activation signal to a detected external electronic device and check human body communication activation status between participating devices by receiving a response to the transmitted signal.

The controller 180 of a mobile terminal may output a first signal through a first electrode to the human body which makes contact to the first electrode S140 and measure a body reception signal of the first signal received by the human body through a second electrode to use the measured body reception signal as a reference signal S150. While extremities of one side of the human body are making contact to the first and the second electrode simultaneously, the controller 180 may output a voltage with a predetermined size and frequency set for measurement of bioelectric impedance through the first electrode and measure a body reception signal of the first signal output to the first electrode through the second electrode.

In general, even if the controller 180 outputs a voltage with a first magnitude is output through a first electrode, the voltage of a first magnitude is not fully received by the human body. In other words, when a first signal having a voltage of the first magnitude is output to the human body through the user's finger while the first electrode makes contact to the finger, voltage attenuation occurs due to contact resistance between the first electrode and skin.

Meanwhile, in the present document, it is assumed that the present invention compensates for the voltage attenuation effect due to contact resistance between the first electrode and skin even if the first electrode outputs a first signal having the first voltage; and defines a signal actually received by the human body as a body reception signal. Accordingly, the first signal output from the first electrode may have different electrical characteristics from those of the body reception signal.

Therefore, it is necessary for the controller 180 to measure a body reception signal which is part of a signal actually received by the human body. In other words, by measuring a body reception signal with respect to a first signal, the controller 180 may obtain a signal input to the extremities of one side of the human body which makes contact to the first and the second electrode. Descriptions of the area in which the first and the second electrode are formed are only an example, and they may be formed on a different surface of a mobile terminal.

The controller 180 may perform measurement by using a body reception signal with respect to a first signal as a reference signal. The reference signal may be used to compare the first signal with the second signal which is the first signal re-transmitted through an external electronic device after the first signal passes through the human body.

In other words, according to one embodiment of the present invention, instead of the first signal delivered to the human body through the first electrode, a body reception signal compensated for the contact resistance between the electrode and skin is used as a reference signal.

After outputting the first signal to the human body making contact to the first electrode and the second electrode, the controller 180 may switch human body communication to the waiting state or inactivation state.

The controller 180 of the mobile terminal may receive an activation signal of human body communication from an external electronic device S160.

When receiving an activation signal of human body communication from an external electronic device, the controller 180 may switch again to the activation state from the waiting or inactivation state.

An external electronic device may obtain a first signal output from a first electrode of the mobile terminal from a first electrode of the external electronic device which makes contact to the extremities in the opposite side of the human body. The external electronic device receives a voltage of a second magnitude which has been attenuated while passing through the human body. At this time, the frequency of a received signal (in what follows, it is called a third signal) is the same as that of the first signal.

When receiving a third signal, an external electronic device may transmit an activation signal of human body communication to the mobile terminal so that the activation state of human body communication may be maintained.

Referring to FIG. 5, after receiving an activation signal of human body communication S160, the controller 180 may compare the received activation signal of human body communication with the activation signal of human body communication transmitted to an external electronic device S161.

More specifically, to activate human body communication, the controller 180 may compare the magnitude of a signal that the mobile terminal has transmitted to the external electronic device with that of a received signal. At this time, the controller 180 may compare magnitude of voltage or current, frequency, or transmission and reception time of the activation signal.

The controller 180 compares individual activation signals and determines a device which has transmitted an activation signal satisfying a predetermined condition as a master device S162. Here, the controller 180 may configure the condition by using magnitude of voltage or current, frequency, or transmission and reception time of an activation signal. For example, the controller 180 may determine a device which provides an activation signal with a large voltage or current as the master device or determine a device which has first transmitted a signal as a master device.

More specifically, while the user holds a first mobile terminal and a second mobile terminal in his both hands, the first and the second mobile terminal may each perform the role of the master device for measuring bioelectric impedance. This is so because both of the first and the second mobile terminal are equipped with an electrode pattern required to measure bioelectric impedance, and accordingly, each mobile terminal may deliver an activation signal for measuring bioelectric impedance to the other mobile terminal.

Here, the activation signal may refer to a signal which triggers the two devices to activate measurement of bioelectric impedance.

Here, a device that delivers the activation signal may be defined as a master device while a device that receives the activation signal output from the master device as a slave device. Therefore, according to the attributes of the activation signal transmitted from the first and the second mobile terminal to their counterpart terminal, one of the two mobile terminals is determined as a master device, and the other mobile terminal is determined as a slave device. When a first mobile terminal is determined as a master device, the first mobile terminal transmits a predetermined electrical signal to a second mobile terminal, where the second mobile terminal analyzes the electrical signal received through the human body and measures bioelectric impedance.

Once a master device is determined, the controller 180 transmits master device information to the counterpart device (slave device) S163 and determines whether a mobile terminal is a master device S164.

If a mobile terminal is determined as a master device from the determination result (Yes in the S164 step), the controller 180 may transmit a control signal to output a specific signal (a fourth signal) to an external electronic device S165.

On the other hand, when a mobile terminal is not a master device (No in the S164 step), the controller 180 may control the mobile terminal to output a specific signal (a fourth signal) S166.

A mobile terminal receives a first signal received from an external electronic device through the human body, which is again transmitted to the human body. And the specific signal (fourth signal) may refer to the signal transmitted to the human body. When a first signal is received through the human body, the mobile terminal may generate the specific signal (fourth signal) by taking into account the signal attenuation ratio so that a signal having the same magnitude as that of a received signal may flow into the human body.

Also, when an external electronic device is determined as a master device, the controller 180 may control the external electronic device to measure bioelectric impedance.

When a mobile terminal is determined as a master device, the controller 180 may provide a guide or an alarm through the display unit 151 or the output unit 150 so that the attitude of the user related to a first extremity unit or a second extremity unit detected by the mobile terminal and the attitude of the user detected by an external electronic device may satisfy a predetermined criterion. For example, the controller 180 may provide a guide or an alarm so that the extremities of the user making contact to the electrodes of a mobile terminal and an external electronic device or the user's body connected to the extremities form an upright position with respect to the user's body.

When a specific signal is output from an external electronic device, the controller 180 may receive, through a second electrode, a second signal from the human body making contact to the second electrode S170.

An external electronic device may output a fourth signal through a second electrode of the external electronic device. At this time, the fourth signal is a signal generated so that a body reception signal becomes the same as a third signal by taking into account a difference between a first signal and a reference signal. Here, the first to the fourth signal are transmitted or received to measure bioelectric impedance and have the same characteristic frequency.

The controller 180 of a mobile terminal may obtain a second signal received through a second electrode of the mobile terminal, where the received second signal is obtained after a fourth signal output from the second electrode of an external electronic device passes through the human body.

The controller 180 of a mobile terminal may measure bioelectric impedance by using a previously obtained reference signal and a second signal S180.

The controller 180 may measure bioelectric impedance by using a difference between a reference signal which is a body reception signal with respect to a first signal and a second signal received through a second electrode of the mobile terminal. Here, bioelectric impedance refers to the total amount of bio-conductive resistance with respect to the alternating current. The bioelectric impedance may be calculated by dividing the difference between a reference signal and a second signal into equal units and dividing the unit by the current value. By applying the bioelectric impedance to various analysis models, body water and body fat may be obtained.

The first and the second electrode of a mobile terminal or an electronic device may be at least one of an antenna area made of a conductive material formed on an area exposed to the outside, front manipulation key, or rear manipulation key; or an electrode formed separately for human body communication.

The first and the second electrode of a mobile terminal or an electronic device may be formed physically by two electrodes. Also, the first and the second electrode of a mobile terminal or an electronic device may be formed by one physical electrode including two areas that may be distinguished from each other.

When the first and the second electrode are formed by one physical electrode, the controller 180 may generate a control signal so that two areas may be switched between a transmission and a reception function.

A mobile terminal or an electronic device may further include a third electrode; when the third electrode detects a touch of the human body, mutual terminal information, human body communication activation signal, and information about the first signal may be transmitted and received through the third electrode. Here, information about the first signal may include information about body reception signal. At this time, the third electrode may be used as a path for transmitting a human body communication activation signal.

When measurement of bioelectrical impedance is completed, the controller 180 may activate the display unit to display bioelectrical impedance. The controller 180 may display the bioelectrical impedance together with analysis results employing the bioelectrical impedance.

When a plurality of external electronic devices is involved, an external electronic device may make contact to other extremities in addition to the first and the second extremity, and the controller 180 may receive a plurality of second signals from the plurality of external electronic devices and measure bioelectrical impedance among extremities by using the plurality of second signals. A method for measuring bioelectrical impedance between external electronic devices or between each external electronic device and a mobile terminal is the same as the method for measuring bioelectrical impedance between a mobile terminal and one external electronic device described above.

FIGS. 6a to 6d illustrate a method for having a mobile terminal related to a first embodiment of the present invention contact an external electronic device.

Referring to FIG. 6a, by contacting a first and a second electrode 132a, 132b of a first mobile terminal 100A simultaneously with a first finger and by contacting a first and a second electrode 123a, 123b of a second mobile terminal 100B simultaneously with a second finger, bioelectrical impedance may be measured through human body communication.

The first and the second electrode 132a, 132b of the first mobile terminal 100A may be installed on an antenna area formed on a side surface of a rear frame and exposed to the outside. Although not shown in detail, like the example of FIG. 2a, the first and the second electrode 132a, I 32b may form an antenna pattern.

Also, a first and a second electrode 123a, 123b of a second mobile terminal 100B may be a rear manipulation key formed on a rear cover of a mobile terminal. In this case, the first and the second electrode 123a, 123b may be formed as one electrode differently from the example of FIG. 2a.

When a portion of the human body contacts the first and the second electrode 132a, 132b of the first mobile terminal 100A and the first and the second electrode 123a, 123b of the second mobile terminal 100B simultaneously, the controllers of the first mobile terminal 100A and the second mobile terminal 100B may switch human body communication into the activation state.

The controller of the first mobile terminal 100A may output a first signal to the human body through the first electrode 132a of the first mobile terminal, obtain a body reception signal received through the human body through the second electrode 132b, and set the body reception signal as a reference signal. After setting a reference signal, the first mobile terminal 100A may switch human body communication to the waiting state or inactivation state.

The controller of the second mobile terminal 100B may receive a third signal which has passed through the human body through the first electrode 123a of the second mobile terminal 100B. When the second mobile terminal 100B receives the third signal, the second mobile terminal 100B may transmit an activation signal to the first mobile terminal 100A to activate human body communication.

When receiving a response to the human body communication activation signal from the first mobile terminal 100A, the controller of the second mobile terminal 100B may generate a fourth signal by using the third signal and output the generated fourth signal through the second electrode 123b of the second mobile terminal 100B. Here, the fourth signal may be the third signal amplified by taking into account the difference between the first signal and the reference signal.

The first mobile terminal 100A may provide bioelectrical impedance by receiving the second signal, which has been output from the first mobile terminal 100B and passed through the human body, and comparing the received second signal with the reference signal.

Referring to FIG. 6b, by contacting a first and a second electrode 132a, 132b of a mobile terminal 100 simultaneously with a first finger and by contacting a first and a second electrode 232a, 232b of an external electronic device 200 simultaneously with a second finger, bioelectrical impedance may be measured through human body communication. Here, the external electronic device 200 may be a camera module that may be combined with a rear surface of the mobile terminal 100.

The first and the second electrode 132a, 132b of the mobile terminal 100 may be installed on an antenna area formed on a side surface of a rear frame and exposed to the outside. Although not shown in detail, like the example of FIG. 2a, the first and the second electrode 132a, 132b may form an antenna pattern.

Also, the first and the second electrode 232a, 232b of the external electronic device 200 may be a conductive material formed on one surface of a camera module that may be combined to the rear surface of the mobile terminal. In this case, different from the example of FIG. 2a, the first and the second electrode 232a, 232b may be formed as one electrode.

When a portion of the human body contacts the first and the second electrode 132a, 132b of the mobile terminal 100 and the first and the second electrode 232a, 232b of the external electronic device 200 simultaneously, the controllers of the mobile terminal 100 and the external electronic device 200 may switch human body communication into the activation state.

The controller of the mobile terminal 100 may output a first signal to the human body through the first electrode 132a of the mobile terminal, obtain a body reception signal received through the human body through the second electrode 132b, and set the body reception signal as a reference signal. After setting a reference signal, the mobile terminal 100 may switch human body communication to the waiting state or inactivation state.

The controller of the external electronic device 200 may receive a third signal which has passed through the human body through the first electrode 232a of the external electronic electrode 200. When receiving the third signal, the external electronic device 200 may transmit an activation signal to the mobile terminal 100 to activate human body communication.

When receiving a response to the human body communication activation signal from the mobile terminal 100, the controller of the external electronic device 200 may generate a fourth signal by using the third signal and output the generated fourth signal through the second electrode 232b of the external electronic device 200. Here, the fourth signal may be the third signal amplified by taking into account the difference between the first signal and the reference signal.

The mobile terminal 100 may receive a second signal which has passed through the human body and compare the received second signal with the reference signal to provide bioelectrical impedance.

Referring to FIG. 6c, by contacting the first and the second electrode 132a, 132b of the mobile terminal 100 simultaneously with a first finger and by contacting the first and the second electrode of an external electronic device 400 simultaneously with the wrist, bioelectrical impedance may be measured through human body communication. Here, the external electronic device 400 may be a watch coupled to the mobile terminal 100.

The first and the second electrode of the external electronic device 400 may be a conductive material formed inside the body of the watch which makes contact to the wrist. In this case, different from the example of FIG. 2a, the first and the second electrode may be formed as one electrode.

When a portion of the human body contacts the first and the second electrode 132a, 132b of the mobile terminal 100 and the first and the second electrode of the external electronic device 400 simultaneously, the controllers of the mobile terminal 100 and the external electronic device 400 may switch human body communication into the activation state.

The controller of the mobile terminal 100 may output a first signal to the human body through the first electrode 132a of the mobile terminal, obtain a body reception signal received through the human body through the second electrode 132b, and set the body reception signal as a reference signal. After setting a reference signal, the mobile terminal 100 may switch human body communication to the waiting state or inactivation state.

The controller of the external electronic device 400 may receive a third signal which has passed through the human body through the first electrode of the external electronic electrode 400. When receiving the third signal, the external electronic device 400 may transmit an activation signal to the mobile terminal 100 to activate human body communication.

When receiving a response to the human body communication activation signal from the mobile terminal 100, the controller of the external electronic device 400 may generate a fourth signal by using the third signal and output the generated fourth signal through the second electrode of the external electronic device 400. Here, the fourth signal may be the third signal amplified by taking into account the difference between the first signal and the reference signal.

The mobile terminal 100 may receive a second signal which has passed through the human body and compare the received second signal with the reference signal to provide bioelectrical impedance.

Referring to FIG. 6d, by contacting the first and the second electrode 132a, 132b of the mobile terminal 100 simultaneously with a first finger and by contacting the first and the second electrodes of a plurality of external electronic devices 200, 300, 400 simultaneously with the wrist and both toes, bioelectrical impedance may be measured through human body communication. Here, the plurality of external electronic devices 200, 300, 400 may be a camera module or an audio module that may be combined to the rear surface of the mobile terminal 100 or a watch or glass that may be coupled to the mobile terminal 100.

The first and the second electrode 132a, 132b of the mobile terminal 100 may be installed on an antenna area formed on a side surface of a rear frame and exposed to the outside. Although not shown in detail, like the example of FIG. 2a, the first and the second electrode 132a, 132b may form an antenna pattern.

Also, the first and the second electrodes of the plurality of external electronic devices 200, 300, 400 may be composed of conductive material formed on at least one surface of each module or electronic device.

When a portion of the human body contacts the first and the second electrode 132a, 132b of the mobile terminal 100 and the first and the second electrodes of the plurality of external electronic devices 200, 300, 400 simultaneously, the controllers of the mobile terminal 100 and the plurality of external electronic devices 200, 300, 400 may switch human body communication into the activation state.

The controller of the mobile terminal 100 may output a first signal to the human body through the first electrode 132a of the mobile terminal, obtain a body reception signal received through the human body through the second electrode 132b, and set the body reception signal as a reference signal. After setting a reference signal, the mobile terminal 100 may switch human body communication to the waiting state or inactivation state.

The controllers of the plurality of external electronic devices 200, 300, 400 may receive a third signal which has passed through the human body through the first electrodes of the plurality of external electronic devices 200, 300, 400. When the plurality of external electronic devices 200, 300, 400 receive the third signal, the plurality of external electronic devices 200, 300, 400 may transmit an activation signal to the mobile terminal 100 to activate human body communication.

When receiving a response to the human body communication activation signal from the mobile terminal 100, the controllers of the plurality of external electronic devices 200, 300, 400 may generate a fourth signal by using the third signal and output the generated fourth signal through the second electrodes of the plurality of external electronic devices 200, 300, 400. Here, the fourth signal may be the third signal amplified by taking into account the difference between the first signal and the reference signal. By comparing the second signal which has passed through the human body with the reference signal, the mobile terminal 100 may provide bioelectrical impedance.

A method for measuring bioelectrical impedance between the mobile terminal 100 and the plurality of external electronic devices 200, 300, 400 may be performed by measuring bioelectrical impedance between the mobile terminal and each external electronic device and measuring bioelectrical impedance between external electronic devices.

FIGS. 7 to 9 illustrate a signal flow for measuring bioelectric impedance according to a method for controlling a mobile terminal according to a first embodiment of the present invention.

FIG. 7 illustrates a method for a mobile terminal related to a first embodiment of the present invention to determine a master device.

Referring to FIG. 7, the mobile terminal 100 and at least one electronic device 200, 300, 400 may transmit and receive an activation signal A1, A2 of mutual human body communication.

When the extremities of the user make contact simultaneously to a first and a second electrode of at least one of the mobile terminal 100 or electronic devices 200, 300, 400, the corresponding device may activate human body communication and transmit an activation signal of human body communication to the other device.

Also, the electronic device 200, 300, 400 which has received the activation signal A1 of human body communication from the mobile terminal 100 may again transmit the activation signal A2 of human body communication to the mobile terminal 100. At this time, the ground voltage of the mobile terminal 100 may differ from that of the electronic device 200, 300, 400.

When transmission and reception of a human body communication activation signal is completed, the mobile terminal 100 or the external electronic device 200, 300, 400 may determine a master device by comparing the transmitted and received activation signal of human body communication and transmit master device information to the counterpart electronic device.

FIGS. 8 to 9 illustrate a method for a mobile terminal related to a first embodiment of the present invention to transmit a signal through an electrode for measuring bioelectrical impedance.

Referring to FIG. 8, the controller 180 of a master device may transmit a first signal S1 to a first extremity of the human body which makes contact to the first electrode 132a of the master device 100, measure a body reception signal R1 of the first signal, and set the measured body reception signal as a reference signal.

In general, the first signal S1 output from the master device 100 flows into the human body after being attenuated by a predetermined factor, and the signal which actually flows into the human body is the body reception signal R1 of the first signal.

The first signal S1 may flow into the first extremity and pass through the human body; the first signal which has passed through the human body may be delivered to an external electronic device 200, 300, 400 through the first electrode 232a, 332a, 432a of the external electronic device 200, 300, 400 which makes contact to a second extremity. Here, the external electronic device 200, 300, 400 may receive a third signal S1', where the third signal is obtained from the first signal S1 output from the master device 100 after the first signal undergoes a predetermined amount of attenuation through the human body. The third signal S1' may be received through the first electrode 232a, 332a, 432a of the external electronic device 200, 300, 400.

Referring to FIG. 9, the controller 180 of the master device 100 detects reception of a second signal S2 through the second electrode 132b. The second signal S2 may be a fourth signal P1 generated at an external electronic device 200, 300, 400, electrically attenuated as the fourth signal passes through the human body through the first electrode 232a, 332a, 432a of the external electronic device 200, 300, 400.

More specifically, the external electronic device 200, 300, 400 may output the fourth signal P1 through the second electrode 232b, 332b, 432b of the external electronic device 200, 300, 400. Also, the first electrode 232a, 332a, 432a of the external electronic device 200, 300, 400 may measure an actual signal R2 which is the fourth signal P1 flowing into the human body through the second extremity.

The controller 180 of the master device 100 may calculate bioelectrical impedance by comparing the received second signal S2 and the reference signal R1 measured in the example of FIG. 7.

FIG. 9 shows a measurement result of bioelectrical impedance performed by a mobile terminal related to a first embodiment of the present invention.

FIG. 10 illustrates an example in which a bioelectric impedance measurement result is displayed according to a first embodiment of the present invention.

Referring to FIG. 10, when detecting contact of the human body through a first and a second electrode, the controller 180 of a mobile terminal activates human body communication and detect an external electronic device capable of performing human body communication.

The controller 180 may display, on the display unit, o AAA and o BBB which are identification information of an external electronic device capable of performing human body communication. And the controller 180 may display a menu by which to select an electronic device to perform human body communication among external electronic devices together with the identification information.

After measuring bioelectrical impedance through human body communication by selecting a specific electronic device among a plurality of detected external electronic devices, the controller 180 may display the measurement result on the display unit 151. At this time, the controller 180 may display a bioelectrical impedance analysis result including muscle content, body fat, and BMI on the display unit 151. Also, a graphic object may be displayed, which indicates whether the measurement result falls within a normal range or lies outside the normal range on the basis of the body information of the user.

Meanwhile, according to one embodiment of the present invention, since bioelectrical impedance is measured by having two electronic devices make contact to a first and a second extremity of the user, the measurement result of bioelectrical impedance may differ according to the length of a path expanding from the first to the second extremity of the user's body. For example, when the user is bending both arms or only one arm, one of the arms makes contact to the user's torso, and the signal transmission path may be split at a particular point.

For example, when there is a split point between the first and the second extremity, the bioelectrical impedance measurement value may reveal different values along the first and the second path with respect to the split point. In this case, since reliability of the measured bioelectrical impedance may become low, at least one of the two electronic devices may output guide information related to the user's attitude.

FIG. 11 illustrates an example of a user's attitude when bioelectric impedance is measured according to a first embodiment of the present invention.

Referring to FIG. 11, a method for a mobile terminal related to a first embodiment of the present invention to guide the user's attitude will be described. It is assumed that the mobile terminal 100 is set as a master device.

Referring to FIG. 11, the controller 180 of a mobile terminal may receive attitude information of the user holding the mobile terminal 100 or an external electronic device 200 detected by the sensing unit of the mobile terminal or external electronic device 200 and provide a guide or an alarm so that the received attitude of the user may satisfy a predetermined criterion.

In other words, there is a need to guide the user's attitude so that the path through which an electrical signal flows between the first and the second extremity is not changed.

However, when a portion of the user's body connected to the first or the second extremity makes contact to the torso, an electrical signal output from the first extremity may flow only through one of the first path P1 or the second path P2, reliability of a measurement result may be degraded.

More specifically, when the controller 180 of the mobile terminal determines that the user holds his or her arms on the torso, a signal output through a first electrode of the mobile terminal may be delivered to the torso after passing through a portion of the arm instead of being delivered across the entire arms of the user. Therefore, the controller 180 may provide a guide or an alarm to the mobile terminal or external electronic device 200 so that the joint portion θ1, θ2 connected to the first or the second extremity may be spread horizontally or vertically.

As shown in FIG. 11(a), when there exists body medium paths P1, P2, and particular points may be used as a split point, the controller 180 may guide the user's attitude so that the body medium paths may be constructed in the form of P3 or P4 as shown in FIG. 11 (b) or (c).

In other words, the smallest value of θ1 has to be larger than zero, and preferably, it may be guided to be 90°. Also, the smallest value of θ2 has to be larger than zero, and preferably, it may be guided to be 180°.

FIGS. 12 to 15 illustrate a method for measuring bioelectric impedance of a particular body area by using two or more different electronic devices according to a first embodiment of the present invention.

Referring to FIG. 12, according to one embodiment of the present invention, depending on the body area to which at least two or more electronic devices make contact, bioelectrical impedance for specific body areas may be measured in more detail.

For example, the body area of the user may be divided into the right arm area B1, left arm area B2, torso area B3, left leg area B4, and right leg area B5.

When only the bioelectrical impedance of the right arm area B1 is needed, two devices are put to make contact to both ends of the B1 area, and a bioelectrical impedance measurement operation according to one embodiment of the present invention is performed, by which the bioelectrical impedance of the right arm area B1 may be known. This operating scenario may be applied in the same way for other areas.

In other words, by extending the method for measuring bioelectrical impedance according to the first embodiment of the present invention, body composition of each body area may be measured in more detail.

FIG. 13 illustrates another method for measuring detailed body composition of each body area.

Referring to FIG. 13, four electronic devices may be arranged to make contact to both hands and both feet. One of the four electronic devices may be set as a master device, and the remaining three electronic devices may be set as a slave device.

More specifically, the first mobile terminal 100A, the second mobile terminal 100B1, the third mobile terminal 100B2, and the fourth mobile terminal 100B3 may be arranged to make contact to both hands and both feet, respectively. Here, the first mobile terminal 100A may be a master device, and the remaining devices 100B1, 100B2, 100B3 may be slave devices.

As shown in FIG. 13(a), when the master device 100A contacts the right hand and outputs a test signal to the other devices 100B1, 100B2, 100B3 through the user's torso, the master device 100A may receive feedback signals which have flown through the user's body respectively from the other devices 100B1, 100B2, 100B3.

In other words, the master device 100A may measure a first body composition signal, which is an accumulated body composition value of the right arm, torso, and left arm, through human body communication with the first slave device 100B1. Also, the master device 100A may measure a second body composition signal, which is an accumulated body composition value of the right arm, torso, and left leg, through human body communication with the second slave device 100B2. Also, the master device 100A may measure a third body composition signal, which is an accumulated body composition value of the right arm, torso, and right leg, through human body communication with the third slave device 100B3. Also, the master device 100A may measure body composition of the user by accumulating the first body composition signal, the second body composition signal, and the third body composition signal, and by using the master device 100A which makes contact to the right hand.

Also, in the cases of FIG. 13(b) to (d), depending on the body area to which the master device 100A makes contact, four different body composition measurements of the user may be obtained. By using the measurement results, body composition values of the right arm, left arm, torso, and right leg may be obtained, respectively.

FIG. 13 illustrates an example in which body composition is measured while a plurality of electronic devices is making contact to the extremities (for example, extremities of the right arm, left arm, right foot, and left foot) of the human body. However, the present invention is not limited to the specific example.

For example, FIG. 14 illustrates an example in which body contact areas to which a plurality of separated devices make contact are further diversified to make body areas for measurement may be further subdivided.

Referring to FIG. 14, the first master device 100A1 and the second master device 100A2 may contact specific areas of the right arm of the user, and the remaining slave devices 100B1, 100B2, 100B3, 100B4, 100B5, 100B6, 100B7, 100B8, 100B9, 100B10, 100B11 are attached to particular areas of the remaining body areas. In this case, when the method for measuring bioelectrical impedance according to one embodiment of the present invention is applied after the first 100A1 and the second master device 100A2 are activated, only the body composition of the lower portion of the right arm may be measured separately.

Referring to FIG. 15, when a mobile terminal 100 and an external electronic device 20 detachable from the mobile terminal are put on the thigh and the knee area respectively, a first signal P1, P2 may be delivered along different body paths depending on the positions of the mobile terminal 100 and the external electronic device 200, and the controller 180 may measure bioelectrical impedance of the delivery paths of the first signal P1, P2.

Therefore, the user may measure bioelectrical impedance by having the first and the second electrode of the mobile terminal or the external electronic device make contact to both extremities of the body desired to be measured.

In other words, according to one embodiment of the present invention, to measure bioelectrical impedance of a desired body area, two electronic devices may be placed at specific positions of the body. Meanwhile, depending on the type of body composition to be measured, an electrical signal transmitted from the first device to the second device may be changed. For example, an electrical signal may be output after the current, voltage, frequency, or magnitude of the electrical signal is changed so that the electrical signal may be appropriate for the body area desired to be measured.

FIG. 16 is a flow diagram illustrating a method for controlling a mobile terminal according to a second embodiment of the present invention, and FIG. 17 illustrates a method for controlling a mobile terminal according to a second embodiment of the present invention.

According to a second embodiment of the present invention, bioelectrical impedance may be measured by using one mobile terminal. At this time, the mobile terminal may be a handheld phone, a watch phone, or a wearable electronic device such as a glass-type mobile terminal.

Referring to FIG. 16, the controller 180 of the mobile terminal may detect contact to the first and the second extremities of the human body simultaneously through the first and the second electrode formed in the mobile terminal S210. Here, the first or the second extremities may represent the extremities of the left-side body and the extremities of the right-side body or the separated extremities of the body. For example, the first extremities may represent the right fingers, and the second extremities may represent the left fingers. Also, the first extremities may represent right thumb, and the second extremities may represent the right index finger.

The controller 180 may activate human body communication when the first and the second electrode of the mobile terminal exposed to the outside make contact to different extremities simultaneously.

The controller 180 may determine whether different extremities of the human body are contacted simultaneously by outputting a specific signal to one of the first or the second electrode and measuring the reception time of the specific signal at the opposite electrode. Whether different extremities of the human body have been contacted simultaneously may be determined by using other sensing information in addition to the method above.

The first electrode or the second electrode may be formed as two electrodes physically separated from each other or as one physical electrode including two distinctive areas. The controller 180 may generate a control signal which switches functions of the first and the second electrodes so that the two electrodes may switch their functions between a transmission and reception function. In particular, when the first and the second electrode are formed as one physical electrode, the controller 180 may control the electrodes so that the two distinctive area may switch their functions between transmission and reception function.

The first electrode and the second electrode may be an antenna area formed to face the outer surface of the side surface of the mobile terminal or a manipulation key formed to face the rear surface of the mobile terminal. At this time, the first and the second electrode may include two or more distinctive electrodes.

When body contact to the first and the second electrode is detected, the controller 180 of the mobile terminal may switch to the operation mode in which human body communication may be performed.

The first and the second electrode of the mobile terminal may be formed in either of the antenna area formed to face the side surface of the mobile terminal and the rear surface manipulation key or may be formed in both areas.

When the first and the second electrode are formed on both the antenna area and the manipulation key, the controller 180 may activate human body communication only when the controller detects contact of the human body to the corresponding antenna area or manipulation key area simultaneously. In other words, when either extremity of the body makes contact to the antenna area and the other extremity makes contact to the rear surface manipulation key, the controller 180 may consider the current arrangement as invalid contact. Descriptions about the areas in which the first and the second electrode are formed are only one example, and the electrodes may be formed in other surfaces of the mobile terminal.

More specifically, when body contact is detected through the manipulation key formed on the rear surface of the mobile terminal, the controller 180 may obtain contact pressure of the body, and when the contact pressure is less than a threshold value, the controller may switch to an operation mode in which human body communication may be performed. In other words, when the contact pressure on the manipulation key formed on the rear surface is less than a threshold value, the controller 180 may recognize that the manipulation key functions as a touch key while, if the contact pressure is larger than the threshold value, the controller 180 may recognize that the manipulation key functions as a push key.

The controller 180 of the mobile terminal may output a first signal to the first extremities making contact to the first electrode S230, measure a body reception signal of the first signal through the first electrode, and set the measured body reception signal as a reference signal S240.

More specifically, when the first and the second electrode are distinguished from each other as a transmitting electrode and a receiving electrode, the controller 180 may output a first signal through the transmitting electrode of the first electrode and measure a body reception signal of the first signal through the receiving electrode of the first electrode. As described above, since all of the first signal output through the transmitting electrode of the first electrode is not delivered to the human body but part of the first signal is reflected away, it is necessary to measure a signal which has been actually received by the human body.

Also, when the first and the second electrode are formed as one electrode, the controller 180 may output a first signal to the first extremity contacted to the first electrode after setting the function of the first electrode as a transmission mode. When the first signal is completely output, the controller 180 may change the function of the first electrode to a reception mode, measure a body reception signal of the first signal through the first electrode, and set the measured body reception signal as a reference signal.

The controller 180 of the mobile terminal may receive a second signal coming from the second extremity contacted to the second electrode S250 and measure bioelectrical impedance by using the reference signal and the second signal S260.

The controller 180 may receive a second signal obtained as the reference signal passes through the human body and is output from the second electrode. The controller 180 may obtain bioelectrical impedance by dividing the difference between the reference signal and the second signal by the current value. Here, the first signal, reference signal, and second signal may be alternating voltage signals having the same specific frequency but with different magnitudes.

When measurement of bioelectrical impedance is completed, the controller 180 may activate the display unit to display bioelectrical impedance. In other words, the controller 180 may measure bioelectrical impedance by maintaining the display unit to the inactivation state while bioelectrical impedance is being measured. Also, the controller 180 may output a measurement result through the sound output unit while maintaining the display unit to the inactivation state.

Referring to FIG. 17, the controller 180 of the mobile terminal may measure bioelectrical impedance through human body communication by having the first and the second electrode make contact to the first and the second extremity simultaneously.

The mobile terminal may be a handheld phone 100 or a bangle-type watch phone 300.

When the mobile terminal is a handheld phone 100, the first electrode may be an antenna area 132a, 132b formed on the first side surface of the mobile terminal, and the second electrode may be an antenna area 132c, 132d formed on the second side surface of the mobile terminal. Also, the first and the second electrode may be a rear surface manipulation key. At this time, when the first and the second electrode include two electrodes respectively, electrode units as shown in FIG. 2b may be formed.

When the mobile terminal is a bangle-type watch phone 300, the first and the second electrode may be formed on the manipulation key 323a, 323b formed on the upper or lower part of the display unit 351. In the same was as described with respect to the rear surface manipulation key, each of the manipulation key 323a, 323b may be formed as two physical electrodes or two separate electrode areas.

The controller 180 may have a finger of the right and left extremities make contact to the first and the second electrode simultaneously (FIG. 13 (a)) or have different fingers of the right or left hand make contact to the first and the second electrode simultaneously (FIG. 13(b) and (c)).

According to the present invention, a function of measuring bioelectrical impedance may be provided by using electrodes formed in a mobile terminal the primary function of which is making a phone call or transmission of messages, an electronic device that may be operated in association with a mobile terminal, or a module detachable from a mobile terminal.

The present invention described above may be implemented in the form of computer-readable program codes in a recording medium in which programs are recorded. The computer-readable recording medium includes all kinds of recording devices storing data that may be read by a computer system. Examples of computer-readable recording media include Hard Disk Drive (HDD), Solid State Disk (SDD), Solid State Drive (SDD), ROM, RAM, CD-ROM, magnetic tape, floppy disk, optical data storage device, and implementation in the form of carrier waves such as transmission through the Internet. Also, the computer may include the controller 180 of a mobile terminal. Therefore, the detailed descriptions above should be regarded as being illustrative rather than restrictive in every aspect. The technical scope of the present invention should be determined by a reasonable interpretation of the appended claims, and all of the modifications that fall within an equivalent scope of the present invention belong to the technical scope of the present invention.

The invention claimed is:

1. A mobile terminal, comprising:
a body;
a first and a second electrode installed respectively at least one side surface of the body and detecting contact of a first body area of a user;
a wireless communication unit transmitting and receiving a first activation signal for human body communication to an external device in contact with a second body area; and
a controller, when a first signal is output to the first body area through the first electrode, measuring a signal compensating for signal attenuation due to contact resistance between the first electrode and the first body area through the second electrode and setting the measured signal as a reference signal; and
when a second signal, which has been generated at the external device and has passed through the user's body, is detected through the second electrode, measuring bioelectric impedance by using the reference signal and the second signal.

2. The mobile terminal of claim 1, wherein the second signal is a fourth signal generated at the external device and subsequently detected through the second electrode after passing through the user's body, and
the fourth signal is a signal generated from the first signal to have the same electric characteristics as those of a third signal which has passed through the user's body and has been detected by an electrode of the external device.

3. The mobile terminal of claim 2, wherein, when the controller senses that the first body area actually makes contact with the first and the second electrode simultaneously, the controller transmits the first activation signal to the external device through the wireless communication unit.

4. The mobile terminal of claim 3, wherein the first activation signal comprises at least one of time, current, voltage, or frequency.

5. The mobile terminal of claim 3, wherein, when receiving a second activation signal for the human body communication from the external device through the wireless communication unit, the controller determines a master device by comparing the first activation signal with the second activation signal and
when the mobile device is determined as the master device, transmits a signal which controls to generate the fourth signal and output the generated fourth signal to the external device.

6. The mobile terminal of claim 1, wherein at least one of the first or the second body area is an extremity of a human body and comprises at least one of arm or leg extremities.

7. The mobile terminal of claim 1, further comprising an interface installed on one side surface of the body and attached to or detached from the external device, wherein, when the external device is coupled through the interface, the controller is configured to function as a single device by the control of a master device.

8. The mobile terminal of claim 1, wherein the wireless communication unit uses one of Body Area Network (BAN), Bluetooth (BT), Bluetooth Low Energy (BLE), and WiFi communication method.

9. The mobile terminal of claim 1, further comprising a sensing unit sensing a user's attitude related to a body part that grips the mobile terminal, wherein the controller outputs guide information so that the user's attitude sensed through the sensing unit satisfies a predetermined criterion.

10. The mobile terminal of claim 9, wherein the controller provides bioelectrical impedance of a specific body area among body areas of the user by combining at least two or more of the plurality of bioelectrical impedance.

11. The mobile terminal of claim 1, wherein, when a plurality of external devices are involved, the controller receives the second signal respectively from a plurality of external devices that make contact with the remaining body areas except for the second body area and measures a plurality of bioelectric impedance by using the reference signal and the plurality of second signals, wherein
the plurality of bioelectric impedance is provided as separate impedance developed between the first body area and the remaining body areas that make contact to the plurality of external devices.

12. The mobile terminal of claim 1, wherein the first and the second electrode correspond to one of an antenna area formed to face one side surface of the body or a manipulation key formed to face a rear surface of the body.

13. The mobile terminal of claim 12, wherein, when the first and the second electrode are formed as one physical electrode, the controller generates a control signal to switch the two distinctive areas between a transmitting and a receiving function.

14. A mobile terminal, comprising:
a first electrode unit;
a second electrode unit; and
a controller, when contact to a first extremity area and a second extremity area of a human body is detected simultaneously through the first and the second electrode unit, switching to an operating mode for performing human body communication, outputting a first signal to the first extremity unit that makes contact to the first electrode unit, measuring a body reception signal of the first signal through the first electrode unit and setting up the measured the body reception signal as a reference signal, receiving a second signal from the second extremity area that makes contact to the second electrode unit, and measuring bioelectric impedance by using the reference signal and the second signal.

15. The mobile terminal of claim 14, wherein the first and the second electrode are formed as two electrodes physically separated from each other or as one physical electrode including two distinctive areas.

16. The mobile terminal of claim 14, wherein the first and the second electrode correspond to one of an antenna area formed to face an outer side surface of a side surface of the terminal or a manipulation key formed to face a rear surface of the terminal.

17. The mobile terminal of claim 16, wherein, when contact of the human body is detected through a manipulation key formed on a rear surface of the terminal, the controller obtains contact pressure of the human body, and when the contact pressure is less than a threshold value, the controller switches to an operating mode in which the human body communication is performed.

18. The mobile terminal of claim 14, wherein the first and the second signal are signals for measuring bioelectrical impedance that generates a current having a specific frequency.

19. The mobile terminal of claim 14, further comprising a display unit; and
when measurement of the bioelectrical impedance is completed, the controller activates the display unit to display the bioelectrical impedance.

20. The mobile terminal of claim 14, wherein, when contact of the human body is detected while a specific application is run, the controller switches to an operation mode in which the human body communication is performed.

* * * * *